(12) United States Patent
Chang

(10) Patent No.: US 12,329,512 B2
(45) Date of Patent: Jun. 17, 2025

(54) TENSION-TYPE SMART SHOE UNIT CAPABLE OF FOOT-PRESSURE MEASUREMENT, CARBON NANOTUBE ALIGNMENT METHOD, SENSOR OF ALIGNED CARBON NANOTUBES AND MANUFACTURING METHOD THEREFOR, SENSOR USING RADIALLY ALIGNED CNT, AND SENSOR ARRAY UNIT

(71) Applicant: CHUNG-ANG UNIVERSITY INDUSTRY-ACADEMIC COOPERATION FOUNDATION, Seoul (KR)

(72) Inventor: Seung Hwan Chang, Seoul (KR)

(73) Assignee: CHUNG-ANG UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 280 days.

(21) Appl. No.: 17/801,008

(22) PCT Filed: Mar. 5, 2021

(86) PCT No.: PCT/KR2021/002730
§ 371 (c)(1),
(2) Date: Aug. 19, 2022

(87) PCT Pub. No.: WO2021/182801
PCT Pub. Date: Sep. 16, 2021

(65) Prior Publication Data
US 2023/0112100 A1 Apr. 13, 2023

(30) Foreign Application Priority Data

Mar. 9, 2020 (KR) .................. 10-2020-0028834
Apr. 22, 2020 (KR) .................. 10-2020-0048427
Sep. 2, 2020 (KR) .................. 10-2020-0111365

(51) Int. Cl.
*A61B 5/103* (2006.01)
*A61B 5/00* (2006.01)
(Continued)

(52) U.S. Cl.
CPC .......... *A61B 5/1038* (2013.01); *A61B 5/6807* (2013.01); *C01B 32/168* (2017.08);
(Continued)

(58) Field of Classification Search
None
See application file for complete search history.

(56) References Cited

U.S. PATENT DOCUMENTS 7,730,547 B2 * 6/2010 Barrera ................. G01L 1/2287
250/306
2009/0302714 A1 * 12/2009 Kim ....................... H10N 30/60
29/25.35
(Continued)

FOREIGN PATENT DOCUMENTS

EP 3 235 428 A1 10/2017
JP 2007-260091 A 10/2007
(Continued)

OTHER PUBLICATIONS

International Search Report for PCT /KR2021/002730 mailed on Jul. 16, 2021.

*Primary Examiner* — Paul M. West
*Assistant Examiner* — Mark A Shabman
(74) *Attorney, Agent, or Firm* — The PL Law Group, PLLC

(57) ABSTRACT

A sensing portion of the tension type smart shoe unit is arranged to extend across the width of thea sole of a wearer so that foot pressure applied through the sole is exerted
(Continued)

thereon, and a connection portion of the tension type smart shoe unit is fixed by connection to a connecting portion of a circuit block. Thus, even when the foot pressure exerted is biased to the left or right while the wearer is walking, only a portion where the pressure is biased is not sensed in contrast with a conventional case in which piezoelectric sensors are mounted, but the sensing portion is deformed, and the magnitude of an electrical output signal corresponding to the deformation is calculated using an equation of a relationship with a load. Consequently, the amount of foot pressure may be precisely measured even with a simple configuration.

5 Claims, 24 Drawing Sheets

(51) Int. Cl.
*B82Y 15/00* (2011.01)
*B82Y 40/00* (2011.01)
*C01B 32/168* (2017.01)
*C09D 183/04* (2006.01)

(52) U.S. Cl.
CPC .... *C09D 183/04* (2013.01); *A61B 2562/0247* (2013.01); *A61B 2562/125* (2013.01); *B82Y 15/00* (2013.01); *B82Y 40/00* (2013.01); *C01B 2202/08* (2013.01); *C01B 2202/22* (2013.01)

(56) References Cited

U.S. PATENT DOCUMENTS

| | | | |
|---|---|---|---|
| 2015/0309563 A1* | 10/2015 | Connor | A61B 5/1071 73/865.4 |
| 2016/0287089 A1* | 10/2016 | Yi | A61B 5/1036 |
| 2017/0331027 A1* | 11/2017 | Kim | H10N 30/098 |
| 2018/0103868 A1* | 4/2018 | Seko | A61B 5/681 |
| 2021/0002816 A1* | 1/2021 | Doshi | A61B 5/112 |

FOREIGN PATENT DOCUMENTS

| | | |
|---|---|---|
| KR | 10-0902081 B1 | 6/2009 |
| KR | 10-2013-0125889 A | 11/2013 |
| KR | 10-1576609 B1 | 12/2015 |
| KR | 10-1658308 B1 | 9/2016 |
| KR | 10-1743915 B1 | 6/2017 |
| KR | 10-2028209 B1 | 11/2019 |
| WO | WO 2004/008095 A2 | 1/2004 |

\* cited by examiner

FIG. 8
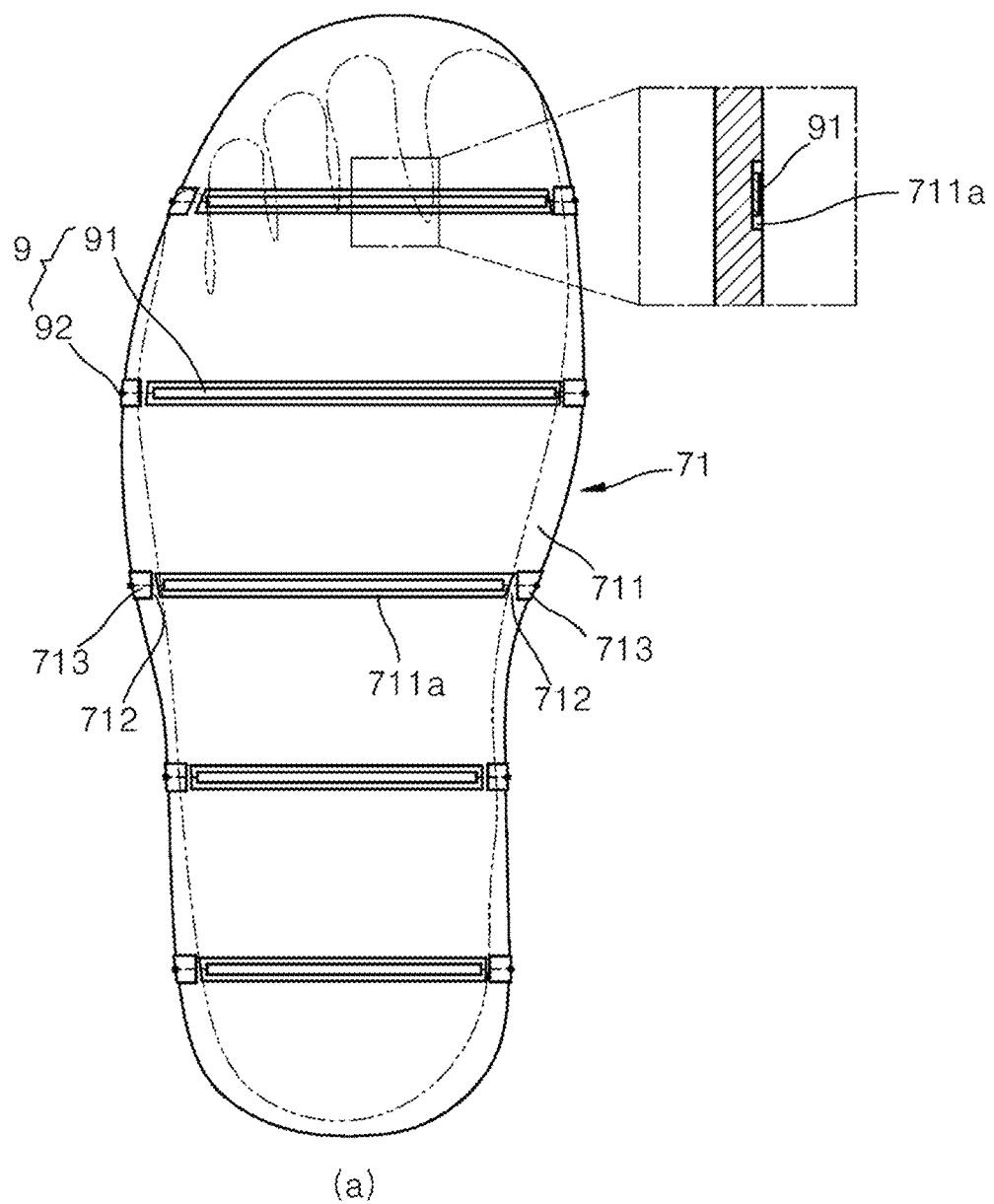
(a)
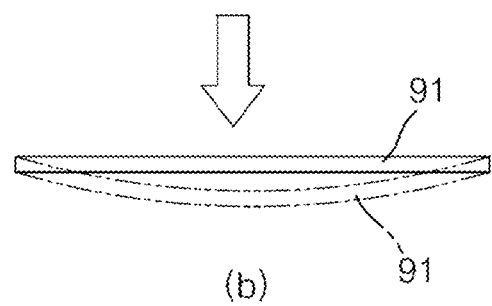
(b)

FIG. 11
S1: PREPARATION OPERATION
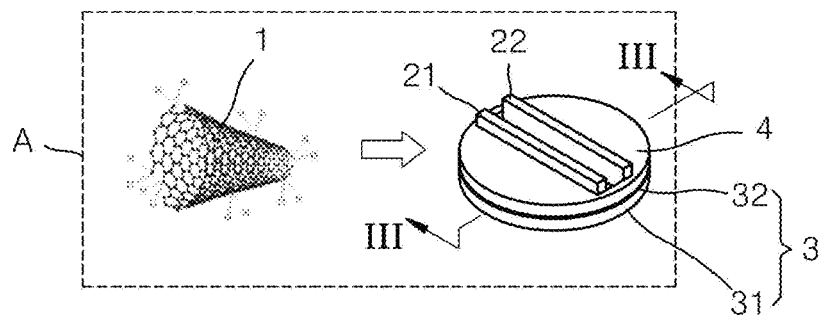
S2: CNT ALIGNMENT OPERATION
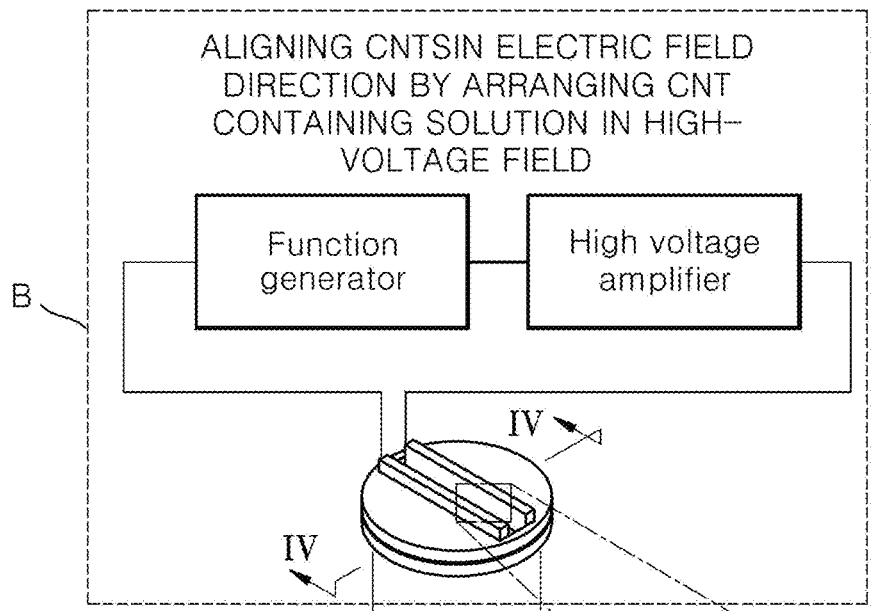
ALIGNING CNTS IN ELECTRIC FIELD DIRECTION BY ARRANGING CNT CONTAINING SOLUTION IN HIGH-VOLTAGE FIELD
S3: SOLUTION REMOVAL OPERATION
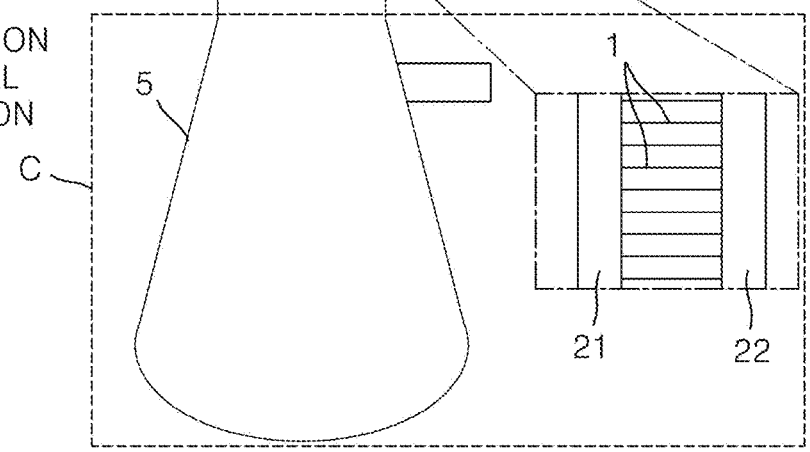

FIG. 28
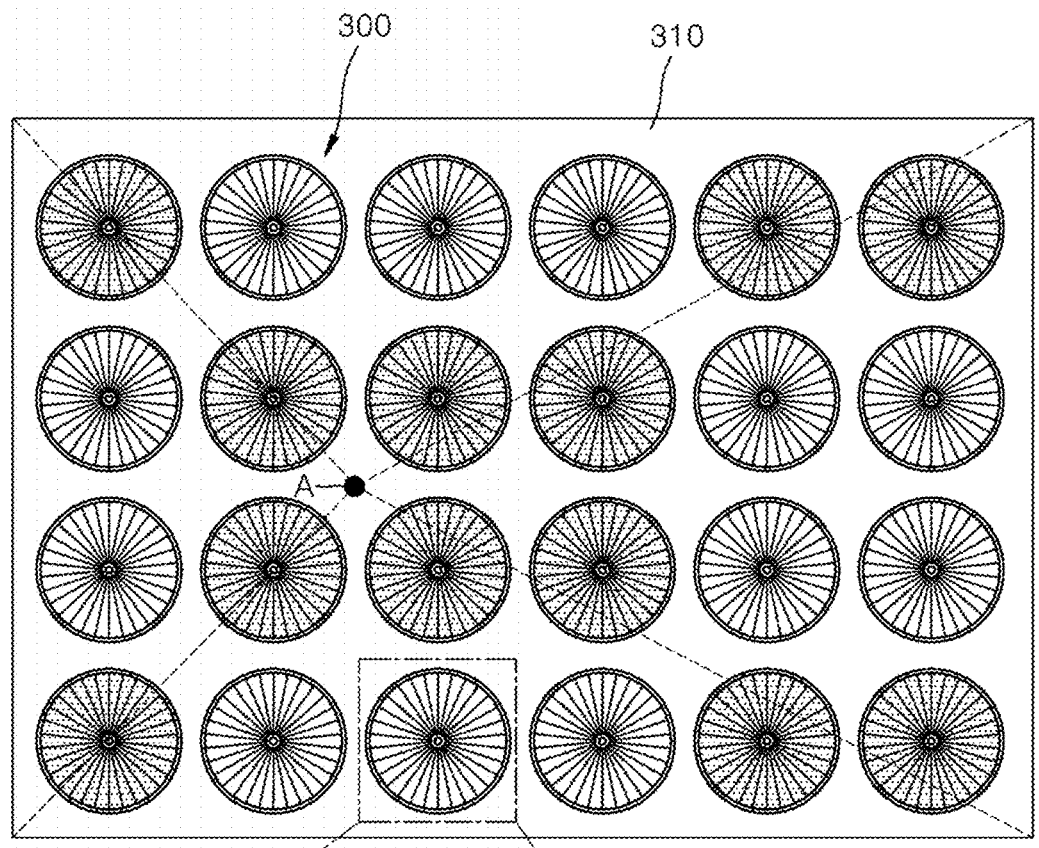
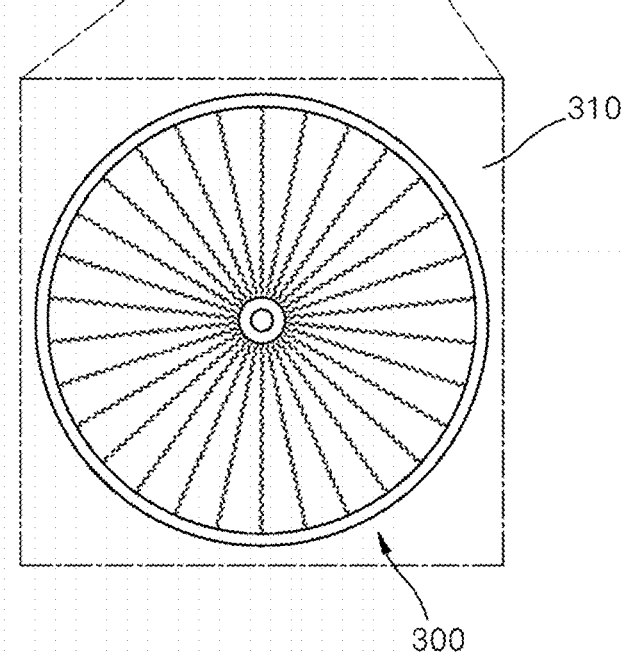

TENSION-TYPE SMART SHOE UNIT CAPABLE OF FOOT-PRESSURE MEASUREMENT, CARBON NANOTUBE ALIGNMENT METHOD, SENSOR OF ALIGNED CARBON NANOTUBES AND MANUFACTURING METHOD THEREFOR, SENSOR USING RADIALLY ALIGNED CNT, AND SENSOR ARRAY UNIT

CROSS REFERENCE TO RELATED APPLICATIONS AND CLAIM OF PRIORITY

This application claims benefit under 35 U.S.C. 119, 120, 121, or 365 (c), Stage entry from International Application No. and is a National PCT/KR2021/002730, filed Mar. 5, 2021, which claims priority to the benefit of Korean Patent Application Nos. 10-2020-0028834 filed in the Korean Intellectual Property Office on Mar. 9, 2020, 10-2020-0048427 filed in the Korean Intellectual Property Office on Apr. 22, 2020 and 10-2020-0111365 filed in the Korean Intellectual Property Office on Sep. 2, 2020, the entire contents of which are incorporated herein by reference.

BACKGROUND

1. Technical Field

1) Tension-Type Smart Shoe Unit Capable of Foot-Pressure Measurement

The present invention relates to a tension-type smart shoe unit capable of foot pressure measurement, and more particularly, to a tension-type smart shoe unit capable of foot pressure measurement, the tension-type smart shoe unit having an improved structure so as to accurately measure a dynamic pressure level during walking or the weight in a stationary state.

2) Carbon Nanotube Alignment Method, Aligned Carbon Nanotube Sensor, and Manufacturing Method Therefor The present invention relates to a carbon nanotube alignment method and an aligned carbon nanotube sensor, and more particularly, to a carbon nanotube alignment method and an aligned carbon nanotube sensor, which enable carbon nanotubes (CNTs) to be aligned in one direction in an electric field and a high-performance sensor function to be realized even with a small number of CNTs.

3) Sensor Using Radially Aligned CNTs and Sensor Array Unit

The present invention relates to a sensor using radially aligned CNTs and a sensor array unit, and more particularly, to a sensor using radially aligned CNTs and a sensor array unit, having an improved structure to enable high-performance realization such as an improvement in sensing sensitivity as impact or pressure sensing is possible at any location on a substrate on which CNTs are placed by radially arranging the CNTs between ring-shaped electrodes, and accurate identification of an impact point at a relatively low cost.

2. Background Art

1) Tension-Type Smart Shoe Unit Capable of Foot-Pressure Measurement

Shoes are one of the most used necessities in our daily life. Energy harvesting technology or walking pattern analysis technology using shoes has been developed because of the frequency of use of shoes as described above. However, most of shoes have a complex structure and low efficiency, and thus many improvements are required until they are manufactured into actual products.

In particular, an existing shoe for foot pressure measurement is configured so that a sensor inserted into an insole can check a pressure signal received from the sole when walking. According to a conventional art, due to a difference in contact pressures between a portion of the insole in direct contact with the sole and a portion of the insole not in contact with the sole, it is possible to compare changes in the distribution of foot pressure in the walking or stationary state, but, due to the limitations of the finite number and distribution of sensors, it is impossible to measure the dynamic pressure level during walking or the weight in a stationary state at a relatively accurate level.

2) Carbon Nanotube Alignment Method, Aligned Carbon Nanotube Sensor, and Manufacturing Method Therefor Carbon nanotubes (CNTs) are minute molecules with a diameter of 1 nanometer (1 nanometer is one billionth of a meter) in which carbons connected by hexagonal rings form a long rod. CNTs, which are cylindrical carbon crystals with a diameter of 0.5 nm to 10 nm, are attracting attention as a next-generation high-tech material because of their high tensile strength and high electrical conductivity, and the strength of CNTs is 100 times superior to steel. These CNTs are attracting attention as a next-generation semiconductor material as it has been found that they have the properties of being either a conductor or a semiconductor depending on the size of the diameter of CNTs, and correspond to a versatile material that is widely used in various fields such as semiconductors, flat panel displays, fuel cells, super-strong fibers, and biosensors.

Recently, a technology for sensing minute movements of the human body or living tissue by using CNTs has been developed, but a large number of CNTs are used to improve sensing precision and sensitivity, and a sensor manufacturing process using CNTs is complicated, which leads to an increase in cost.

3) Sensor Using Radially Aligned CNTs and Sensor Array Unit

CNTs are minute molecules with a diameter of 1 nanometer (1 nanometer is one billionth of a meter) in which carbons connected by hexagonal rings form a long rod. CNTs, which are cylindrical carbon crystals with a diameter of 5 nm to 10 nm, are attracting attention as a next-generation high-tech material because of their high tensile strength and high electrical conductivity, and the strength of CNTs is 100 times superior to steel. These CNTs are attracting attention as a next-generation semiconductor material as it has been found that they have the properties of being either a conductor or a semiconductor depending on the size of the diameter of CNTs, and correspond to a versatile material that is widely used in various fields such as semiconductors, flat panel displays, fuel cells, super-strong fibers, and biosensors.

Techniques have been developed to align these CNTs in one direction and use them as sensors. However, only one direction sensing is not useful, so there is a need to develop technologies capable of replacing, for example, a relatively expensive Rosette strain gage, by enabling sensing by 360 degrees in various directions.

Recently, research and development on sensor technology for measuring a movement state of a human body and bio-signals by attaching a sensor to the human body has been being actively conducted. However, most developed sensor technologies are to attach at least three or more common unidirectional sensors in each of multiple directions to measure a body movement state or bio-signals, and accordingly a technology of enabling multidirectional sensing with one sensor needs to be developed.

SUMMARY

1) Tension-Type Smart Shoe Unit Capable of Foot-Pressure Measurement

Provided is a tension-type smart shoe unit capable of foot pressure measurement, by which a dynamic pressure level during walking or the weight in a stationary state may be accurately measured.

2) Carbon Nanotube Alignment Method, Aligned Carbon Nanotube sensor, and manufacturing method therefor Provided is a carbon nanotube alignment method that enables CNTs to be aligned in one direction in an electric field and high-purity CNTs not affected by polarity in an alignment process and containing no foreign materials to be manufactured.

Provided is a method for manufacturing an aligned carbon nanotube sensor that enables mass production and cost reduction of products by increasing the efficiency of a manufacturing process of a sensor structure using CNTs.

Provided is an aligned carbon nanotube sensor that enables improvements in sensing sensitivity and precision even with a small number of CNTs and enables a simplification of the structure.

3) Sensor Using Radially Aligned CNTs, and Sensor Array Unit

Provided is a sensor using radially aligned CNTs, by which impact or pressure sensing is enabled at any location on a substrate on which CNTs are placed, leading to an improvement in sensing sensitivity, and the sensor is used in a wearable device to measure bio signals and detect the motion state of a human body with high sensitivity in real time, and a sensor array unit.

Provided is a sensor using radially aligned CNTs, which may be manufactured at a relatively low cost and capable of high-performance realization such as accurately identifying an impact point, and a sensor array unit.

4) Tension-Type Smart Shoe Unit Capable of Foot-Pressure Measurement

According to an aspect of the present invention, a tension-type smart shoe unit capable of foot pressure measurement includes a shoe on which a circuit block is installed; and a sensor unit including a material whose impedance or capacitance changes according to deformation and configured to sense static deformation, the sensor unit including a sensing portion formed in the shape of a ribbon or fiber bundle and extending in one of a width direction of covering the foot width of a wearer of the shoe and a length direction of covering the foot length of the wearer of the shoe so as to be deformed by a load of the wearer of the shoe, and connection portions connected to both sides of the sensing portion, respectively, and electrically connected to the circuit block installed on the shoe, to transmit an electrical signal according to the degree of deformation corresponding to the load of the wearer of the shoe to a controller of the circuit block.

The sensor unit may be arranged in plurality at intervals in the lengthwise direction of the shoe when the sensor unit is arranged to extend in the width direction to cover the foot width of the wearer, and may be arranged in plurality at intervals in the width direction of the shoe when the sensor unit is arranged to extend along the foot length of the wearer.

The sensing portion of the sensor unit may be disposed between an insole and a midsole of the shoe.

5) Carbon Nanotube Alignment Method, Aligned Carbon Nanotube Sensor, and Manufacturing Method Therefor According to an aspect of the present invention, a carbon nanotube alignment method includes a preparing operation of accommodating a CNT-containing solution in a space between a pair of electrodes and a substrate on which the electrodes are placed; a CNT alignment operation of aligning CNTs contained in the CNT-containing solution in the direction of an electric field by applying a voltage to the electrodes to form the electric field; and a solution removal operation of removing a liquid solution except for particulate CNTs from the CNT-containing solution so that only the aligned CNTs remain on the substrate.

The substrate may include a base member and a filter paper disposed on the base member to be placed at a location where the filter paper may come into contact with the CNT-containing solution, and the preparation operation may include a vacuum formation operation of forming a vacuum between the base member and the filter paper by using a vacuum pump.

The CNT-containing solution may include deionized water, and the solution removal operation may include a deionized water removal operation of removing the deionized water by using the vacuum pump so that only the aligned CNTs may remain on the filter paper, in a state in which the voltage is released after the CNT alignment operation.

The CNTs contained in the CNT-containing solution may be less than 0.02 wt %.

One of the pair of electrodes may be in the shape of a circular ring, and the other may be disposed in the center of the circular ring, so that the direction of the electric field may be radially formed.

According to an aspect of the present invention, a method of manufacturing an aligned carbon nanotube sensor includes an elastomer coating operation of placing, on a mold, a filter paper on which CNTs are aligned and coating a liquid elastomer; a CNT transfer operation of transferring CNTs to the elastomer cured after being coated and removing the filter paper; and an electrode forming operation of forming an electrode to enable the voltage to be applied from the outside to both ends of the CNTs stacked on the elastic polymer.

The method of manufacturing an aligned carbon nanotube sensor may include an elastomer coating operation of placing, on a mold, a filter paper in which CNTs are aligned in one direction and coating a liquid elastomer; a CNT transfer operation of transferring CNTs to the elastomer cured after being coated and removing the filter paper; and an electrode forming operation of forming an electrode to enable the voltage to be applied from the outside to both ends of the CNTs stacked on the elastic polymer.

The method of manufacturing an aligned carbon nanotube sensor may include a sandwich structure formation operation of forming an additional elastic polymer on the opposite side of the former elastic polymer with the CNTs between the two elastic polymers through a curing process after PDMS coating.

According to an aspect of the present invention, an aligned carbon nanotube sensor includes an elastic polymer formed of an elastically deformable material; and a CNT unit including a plurality of CNT monomers that are placed on the elastic polymer at intervals from each other while being aligned and ribbon-type conductors connected to both ends of the CNT monomers so that the CNT monomers may be connected to an electrode.

The aligned carbon nanotube sensor may further include another elastic polymer for forming a sandwich structure together with the former elastic polymer by being provided on the opposite side of the former elastic polymer with the CNTs between the two elastic polymers.

The aligned carbon nanotube sensor may include a first layer unit including a pair of elastic polymers and CNT monomers provided between the pair of elastic polymers; and one or more second layer units stacked on the first layer unit, having a same configuration as the first layer unit, and including CNT monomers arranged in a different direction from the alignment direction of the CNT monomers of the first layer unit.

6) Sensor Using Radially Aligned CNTs, and Sensor Array Unit

According to an aspect of the present invention, a sensor using radially aligned CNTs includes an inner electrode arranged at the center of an arbitrary circle; an outer electrode spaced apart from the inner electrode in a radial direction to be arranged on the circumference of the circle; and a plurality of CNT units disposed between the inner electrode and the outer electrode, including CNT monomers arranged in the radial direction, and radially arranged in a circumference direction.

The CNT unit may further include PEDOT:PSS, which is a conductive material.

The outer electrode may be in the shape of a long ring extending in the circumference direction.

The outer electrode may include a plurality of electrode elements arranged apart from each other in the circumference direction.

7) Tension-Type Smart Shoe Unit Capable of Foot-Pressure Measurement

In a smart shoe unit capable of foot-pressure measurement, having such a structure as described above, according to the present invention, a main body portion of a sensor is arranged to extend across the width of the sole of a wearer so that foot pressure applied through the sole of the wearer is exerted thereon, and a connection portion of the sensor is fixed by connection to a connecting portion of a circuit block, and thus, even when the foot pressure exerted is biased to the left or right while the wearer is walking, only a portion where the pressure is biased is not sensed in contrast with a conventional case in which a plurality of piezoelectric sensors are mounted, but the main body portion of the sensor composed of a single unit is deformed, and the magnitude of an electrical output signal corresponding to the deformation is calculated using an equation of a relationship with a load. Consequently, the amount of foot pressure may be precisely measured even with a simple configuration.

8) Carbon Nanotube Alignment Method, Aligned Carbon Nanotube Sensor, and Manufacturing Method Therefor In a carbon nanotube alignment method according to the present invention having a configuration as described above, after a CNT-containing solution is accommodated in a space between a pair of electrodes and a substrate, an electric field is formed to align CNTs in an electric field direction, and then the solution is removed so that only the aligned CNTs remain on the substrate, and thus the CNTs may be aligned in a desired direction by variously changing the installation location of an electrode and the intensity of the electric field even with a simple configuration.

In a carbon nanotube sensor manufacturing method according to the present invention having a configuration as described above, an elastomer is coated on a filter paper in which aligned CNTs remain, and is cured, the CNTs are transferred to the cured elastomer, and then electrodes are formed at both ends of the CNTs, and thus a sensor that transmits an electrical signal according to deformation may be manufactured, whereby its manufacturing process may be simplified and its manufacturing costs may be reduced due to use of only a small number of CNTs, matching of the alignment direction of the CNTs with the deformation direction of the elastomer enables implementation of a precise sensing function, and a filter function according to a measurement direction may also be implemented by preventing sensing in a direction orthogonal to the alignment direction.

9) Sensor Using Radially Aligned CNTs, and Sensor Array Unit

In a sensor using radially aligned CNTs according to the present invention having a configuration as described above, one of electrodes is disposed on the center of a circle, the other is disposed on a circumferential line of the circle, and CNT units in which CNT monomers are long connected in a radial direction are radially arranged between a pair of electrodes, and thus, when an impact or pressure is applied to any location on an applied structure (sensor attachment target), as the CNT monomers together with the structure are deformed, electrical signals may be transmitted by the radially arranged CNT units, which leads to an improvement in sensing sensitivity.

In addition, the present invention is configured such that sensing of deformation in the radial direction, which is the arrangement direction of CNT monomers, is possible, but sensing of deformation in the circumferential direction is not possible, and thus, when sensing precision in a specific direction is required, as a disturbance signal detected in another direction is fundamentally blocked, a customized sensor capable of detecting a signal only in a required sensing direction may be manufactured.

BRIEF DESCRIPTION OF THE DRAWINGS

1) Tension-Type Smart Shoe Unit Capable of Foot-Pressure Measurement

FIG. 8 is a bottom view of a combined state of an insole and a sensor unit employed in a tension-type smart shoe unit capable of foot pressure measurement according to another embodiment of the present invention.

2) Carbon Nanotube Alignment Method, Aligned Carbon Nanotube Sensor, and Manufacturing Method Therefor

FIG. 11 is a view for explaining respective implementation processes of operations constituting the carbon nanotube alignment method according to an embodiment of the present invention.

3) Sensor Using Radially Aligned CNTs, and Sensor Array Unit

Figure 23:
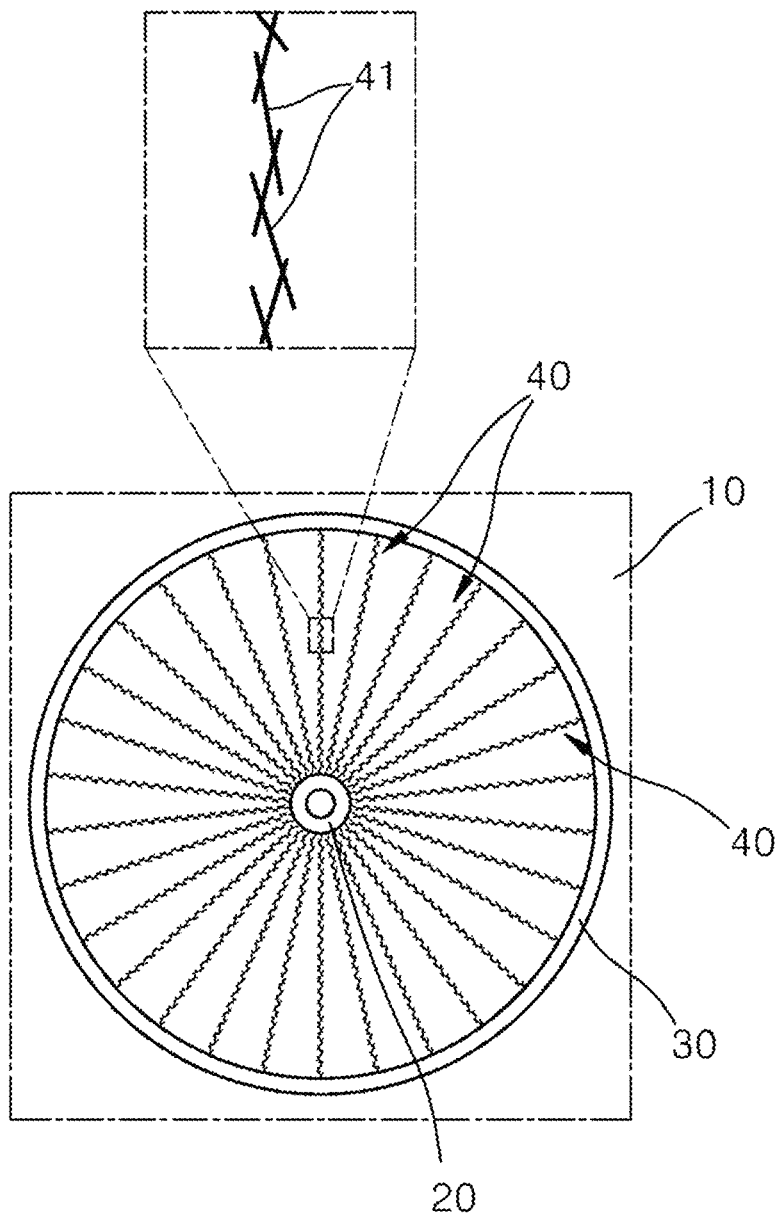

FIG. 23 is a plan view showing the structure of a sensor using radially aligned CNTs according to an embodiment of the present invention.

Figure 24:
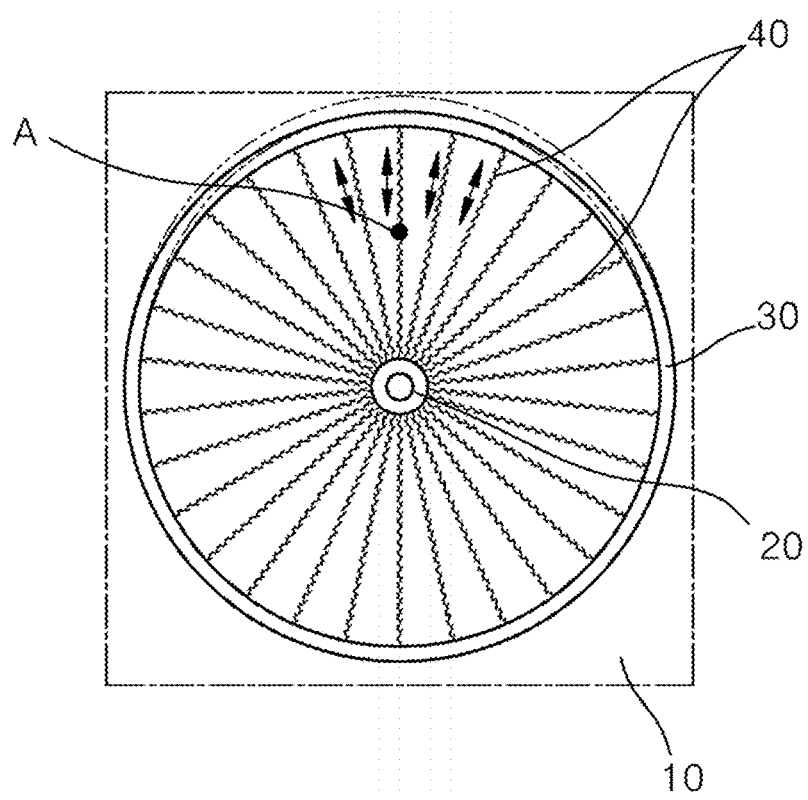

FIG. 24 is an operation state view of an embodiment of the present invention.

Figure 25:
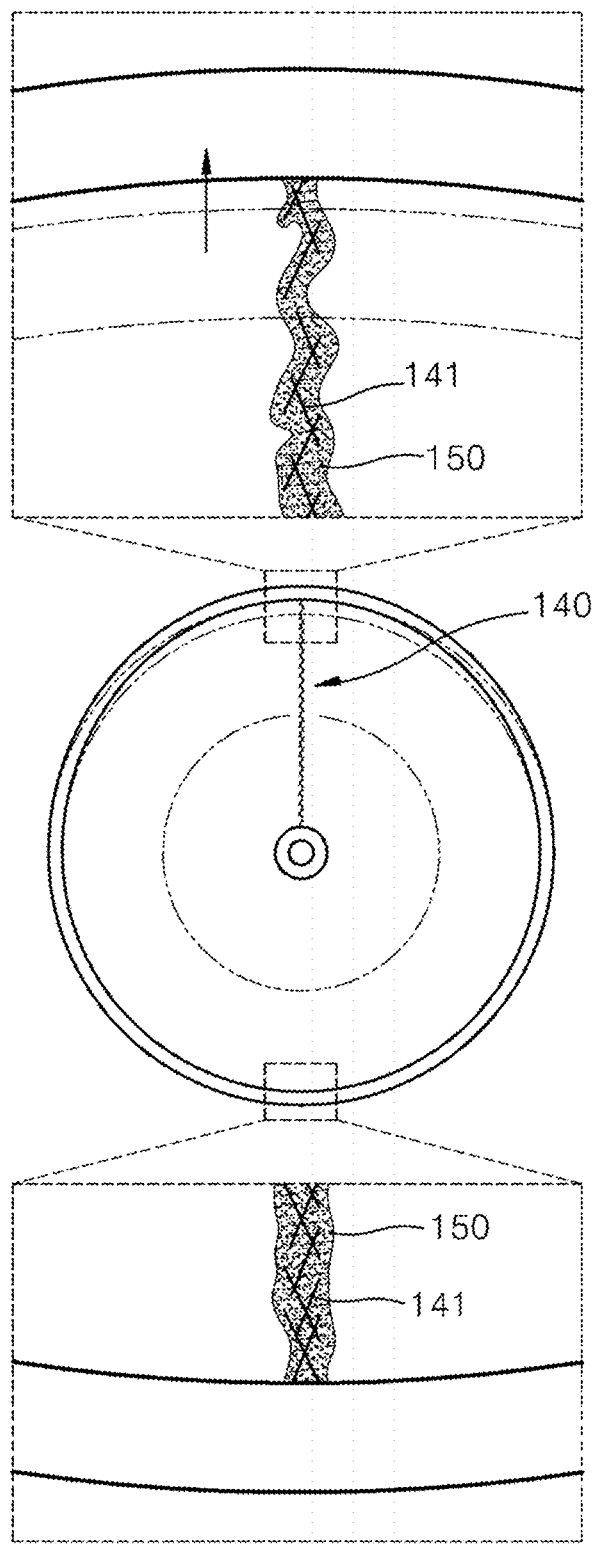

FIG. 25 is a view for explaining an operation and merits of a sensor using radially aligned CNTs according to another embodiment of the present invention.

Figure 26:
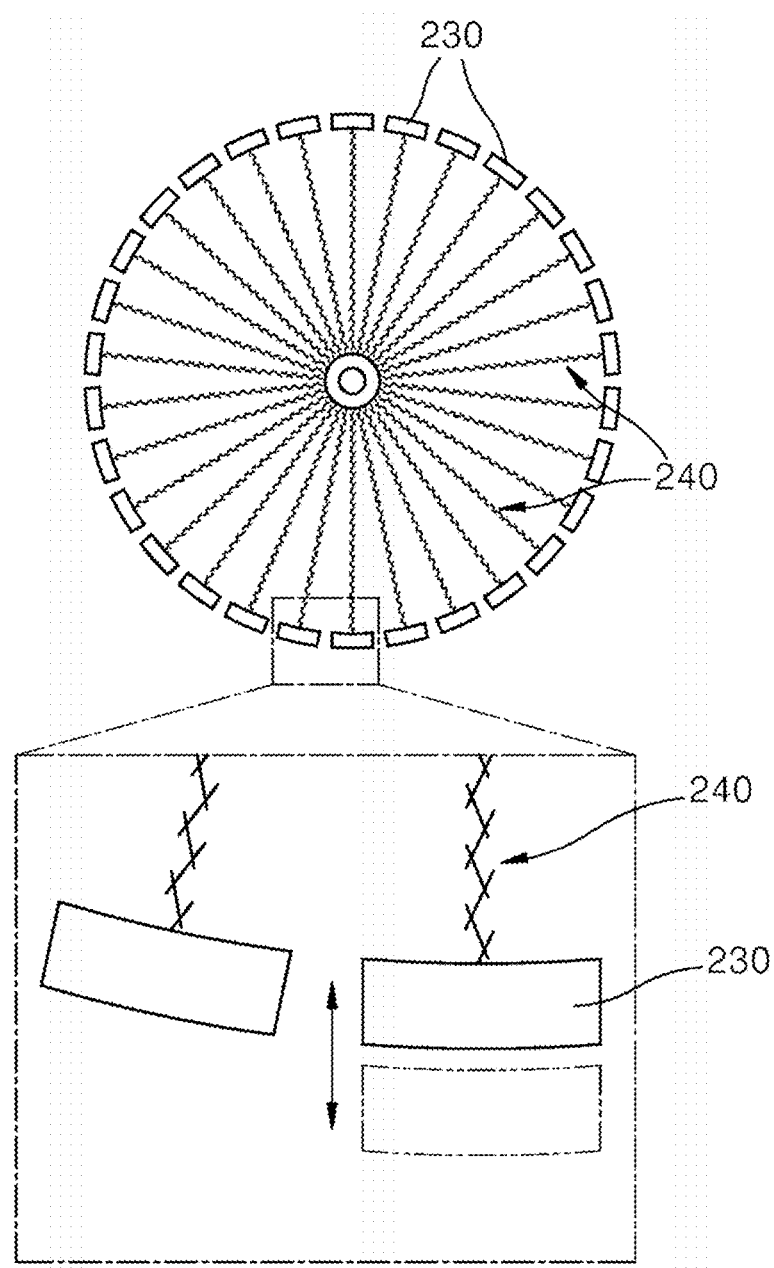

FIG. 26 is a plan view of a sensor using radially aligned CNTs according to another embodiment of the present invention.

Figure 27:
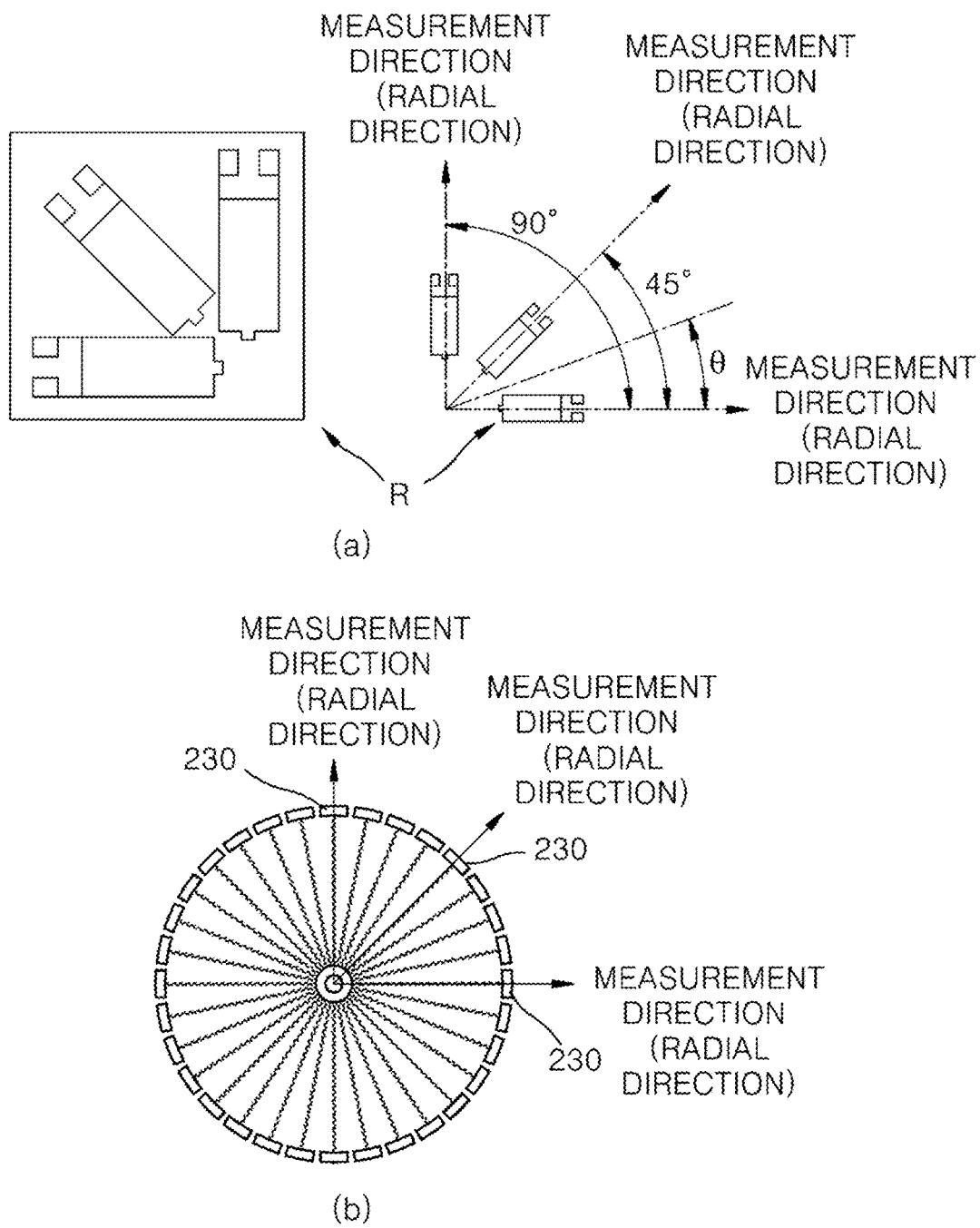

FIG. 27 is a view for explaining merits of another embodiment of the present invention.

FIG. 28 is a view for explaining a structure of a sensor array unit using radially aligned CNTs, according to an embodiment of the present invention.

Figure 29:
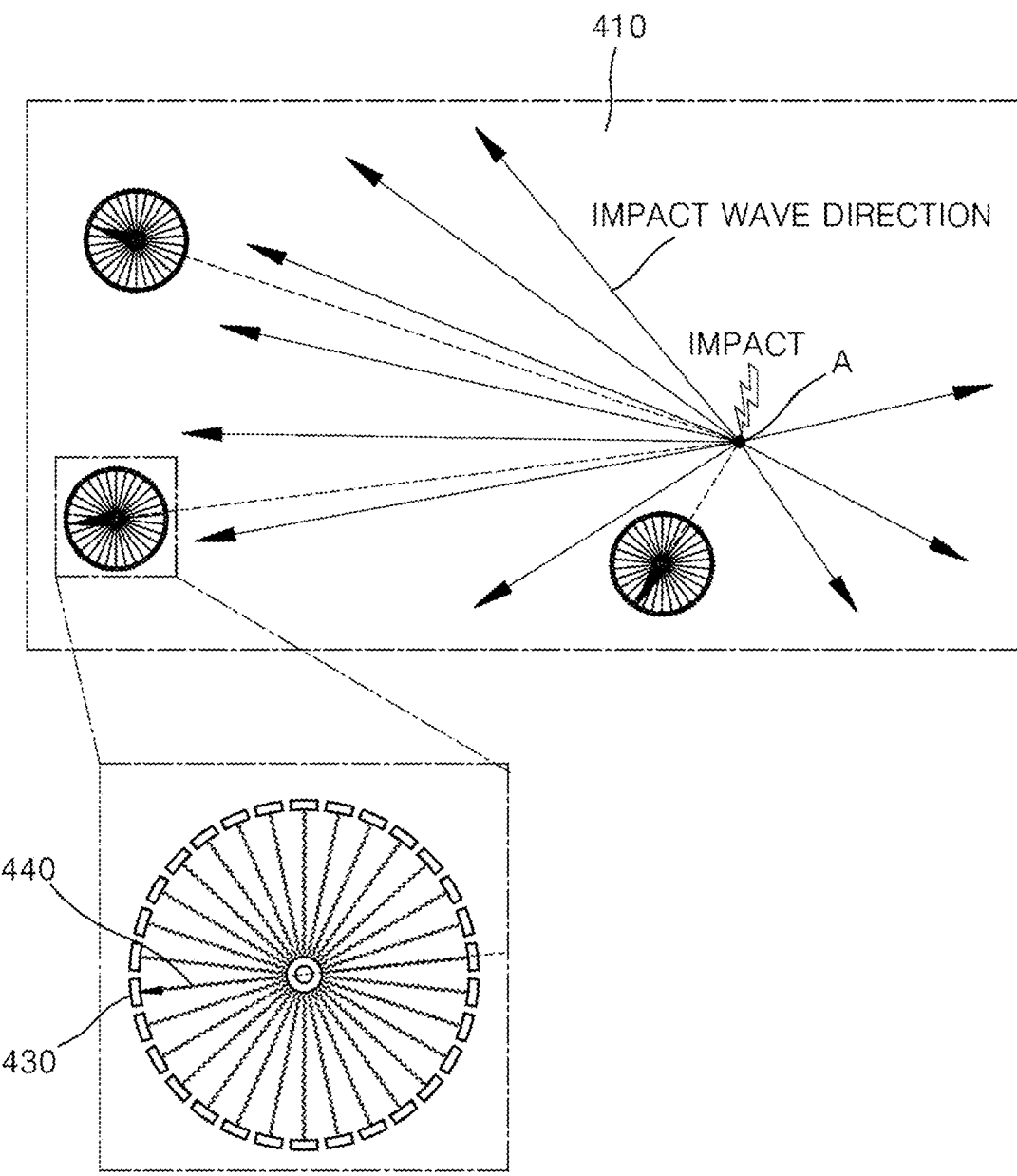

FIG. 29 is a view for explaining a structure of a sensor array unit using radially aligned CNTs, according to another embodiment of the present invention.

DETAILED DESCRIPTION

1) Tension-Type Smart Shoe Unit Capable of Foot-Pressure Measurement

In the following description, in order to clarify the understanding of the present invention, descriptions of well-known technologies for the features of the present invention will be omitted. The following embodiment are detailed descriptions to help the understanding of the present invention, and it will be understood that the scope of the present invention is not limited. Accordingly, an equivalent invention that performs the same function as the present invention will also fall within the scope of the present invention.

In addition, in the following description, the same reference numerals or symbols means the same configuration, and unnecessary redundant description and description of known technology will be omitted. Moreover, a description of each embodiment of the present invention that overlaps with the description of the technology that is the background of the present invention will also be omitted.

Prior to a detailed description of the present embodiment, the structure of a shoe will be briefly described as follows.

In other words, the shoe consists of several components, but largely includes an outsole contacting a bottom surface of the shoe, an insole contacting a wearer's foot, a midsole disposed between the outsole and the insole, an upper that covers a remaining portion except for the wearer's ankle, and a tongue member disposed inside the upper to protect the top of the wearer's foot. According to the present embodiment, an inner portion (portion in contact with the wearer's foot) of the upper is referred to as a lining.

A tension-type smart shoe unit capable of foot pressure measurement according to an embodiment of the present invention will now be described in detail with reference to the accompanying drawings.

Figure 1:
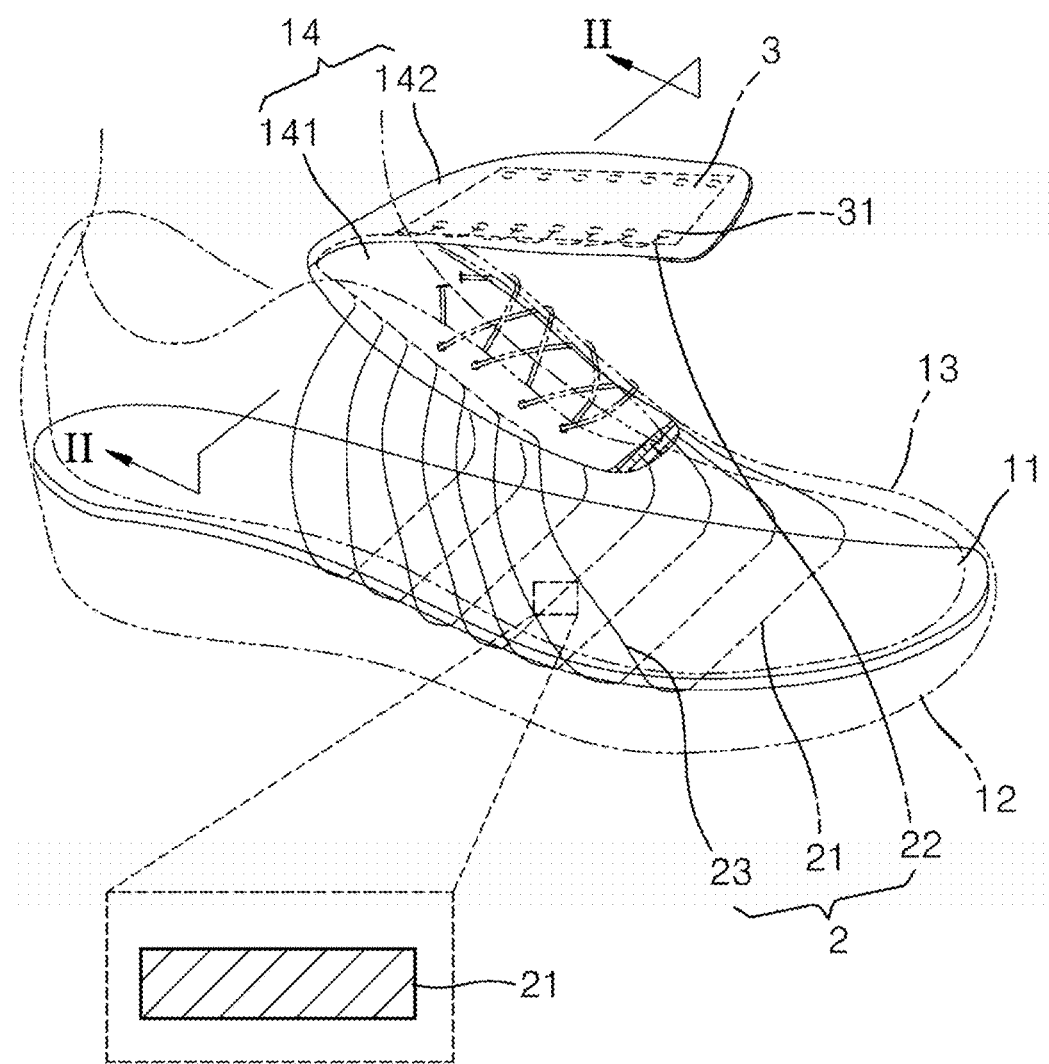
FIG. 1 is a perspective view of a tension-type smart shoe unit capable of measuring foot pressure, according to an embodiment of the present invention.
Figure 2:
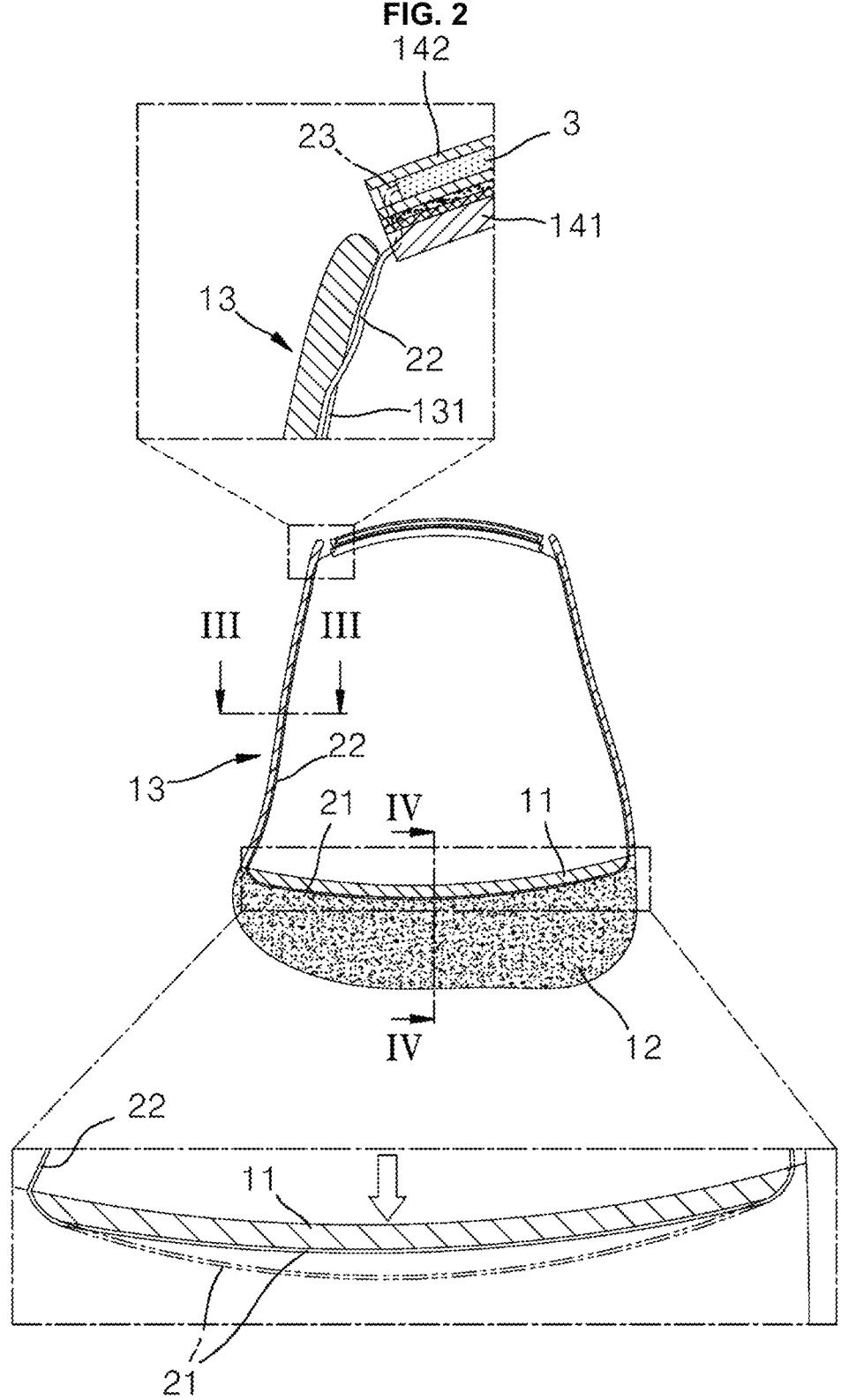
FIG. 2 is a cross-sectional view taken along line II-II of FIG. 1.
Figure 3:
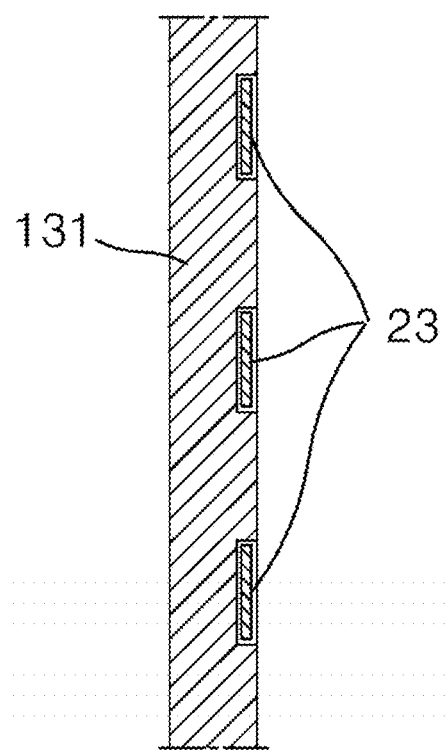
FIG. 3 is a cross-sectional view taken along line III-III of FIG. 2.
Figure 4:
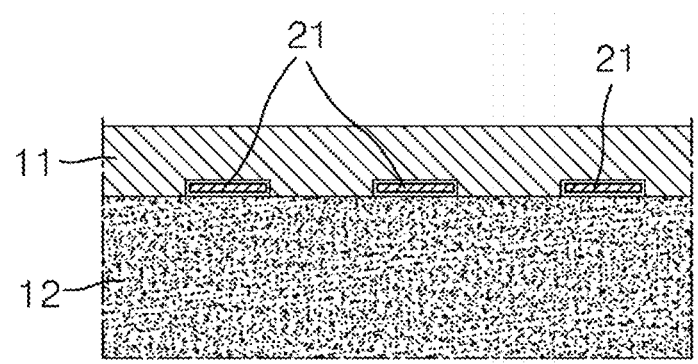
FIG. 4 is a cross-sectional view taken along line IV-IV of FIG. 2.
Figure 5:
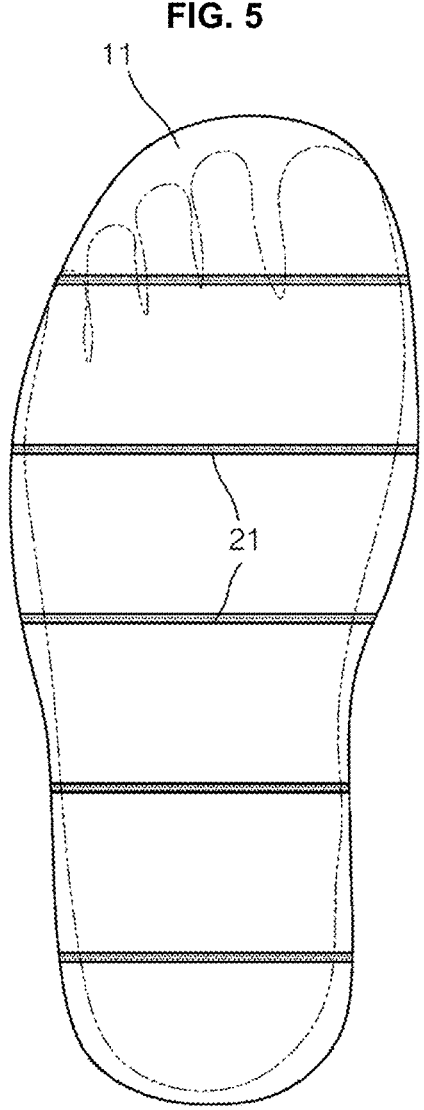
FIG. 5 is a view for explaining the arrangement structure of a sensing portion constituting a sensor unit employed in an embodiment of the present invention.
Figure 6:
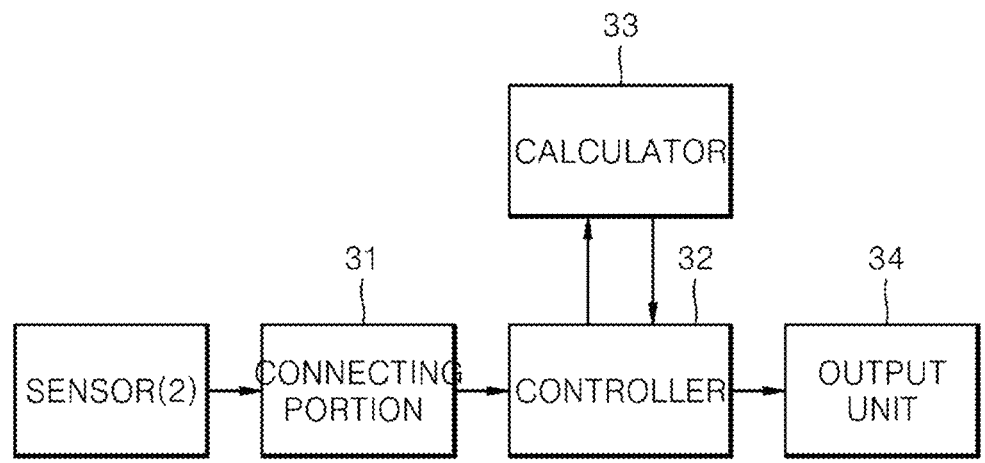
FIG. 6 is a block diagram of the configuration of a circuit block employed in an embodiment of the present invention.

FIG. 1 is a perspective view of a tension-type smart shoe unit capable of foot pressure measurement, according to an embodiment of the present invention. FIG. 2 is a cross-sectional view taken along line II-II of FIG. 1. FIG. 3 is a cross-sectional view taken along line III-III of FIG. 2. FIG. 4 is a cross-sectional view taken along line IV-IV of FIG. 2. FIG. 5 is a view for explaining the arrangement structure of a sensing portion constituting a sensor unit employed in an embodiment of the present invention. FIG. 6 is a block diagram of the configuration of a circuit block employed in an embodiment of the present invention.

As shown in FIGS. 1 and 2, the tension-type smart shoe unit capable of foot pressure measurement according to an embodiment of the present invention includes a shoe 1 mainly worn when walking in daily life, and a sensor unit 2 installed on the shoe 1 to precisely measure a walking pattern or weight of a wearer of the shoe 1.

The shoe 1 is provided with a circuit block 3 for receiving a signal from the sensor unit 2 and calculating the distribution or size of a foot pressure. As well shown in FIG. 6, the circuit block 3 may include a connecting portion 31 to which the sensor unit 2 is connected, a controller 32 that receives a signal of the sensor unit 2 transmitted through the connecting portion 31 and applies a control command for wearer's walking pattern analysis or precise weight measurement, a calculator 33 for calculating a distribution or size of foot pressure, based on a control signal of the controller 32, and an output unit 34 for outputting a result of the calculation, based on the control signal of the controller 32.

The output unit 34 may be configured to output light or sound, and, when a transmitter for wirelessly transmitting a signal is provided in the circuit block 3, the output unit 34 may be configured to transmit the data output to the wearer's mobile phone terminal or a manager server in a wireless communication method.

The sensor unit 2 includes, for example, a material whose impedance or capacitance is changed by deformation, such as PDMS (acrylic polymer) containing an electrically conductive material such as carbon black (electrically conductive material), to sense a static strain. The sensor unit 2 is preferably formed in a long ribbon or fiber bundle form.

The sensor unit 2, as well shown in FIG. 5, includes a sensing portion 21 extending in a width direction to cover the foot width of a shoe wearer and thus being deformed in the width direction of the shoe 1 due to the load of the wearer of the shoe 1, and a connection portion 22 connected to either side of the sensing portion 21 and electrically connected to the circuit block 3 installed on the shoe 1, and transmits an electrical signal according to the degree of deformation of the sensing portion 21 corresponding to the weight of the shoe wearer to the controller 32 of the circuit block 3.

As described above with reference to FIG. 5, a plurality of sensing portions of the sensor unit 2 may each extend in the width direction covering the foot width of the shoe wearer and may be arranged at intervals in the length direction of the shoe. However, a plurality of sensing portions of the sensor unit 2 may each extend in the length direction covering the foot length of the shoe wearer and may be arranged at intervals in the width direction of the shoe.

In the tension-type smart shoe unit capable of foot-pressure measurement, according to an embodiment of the present invention, having the above-described structure, as well shown in FIG. 5, the sensing portion 21 of the sensor unit 2 is arranged to extend across the width of the sole of the wearer so that foot pressure applied through the sole of the wearer is exerted thereon, and the connection portion 22 of the sensor unit 2 is fixed by connection to the connecting portion 31 of the circuit block 3, and thus, even when the foot pressure exerted is biased to the left or right while the wearer is walking, only a portion where the pressure is biased is not sensed in contrast with a conventional case in which a plurality of piezoelectric sensors are mounted, but the sensing portion 21 of the sensor unit 2 composed of a single unit is deformed, and the magnitude of an electrical output signal corresponding to the deformation is calculated using an equation of a relationship with a load. Consequently, the amount of foot pressure may be precisely measured even with a simple configuration.

As shown in FIGS. 1 and 4, the sensor unit 2 exhibiting these advantages is preferably arranged in plurality at intervals in the length direction of the shoe 1. According to this embodiment, the size of the foot pressure of a portion where each sensor unit 2 is installed may be calculated, and consequently the weight of the wearer applied to the entire sensing portion 21 may be precisely measured by adding a load corresponding to the calculated foot pressure of each portion, and also the walking pattern of the wearer may be precisely analyzed by analyzing the distribution of foot pressure in the length direction of the shoe 1.

As shown in FIGS. 2 and 4, the sensing portion 21 of the sensor unit 2 may be disposed between an insole 11 and a midsole 12 of the shoe 1 so that the wearer's load is smoothly transmitted to the side of the sensing portion 21 through the insole 11. However, the present invention is not limited thereto. For example, the sensing portion 21 may be configured to be embedded in the insole or may be configured to be embedded in the midsole.

The sensor unit 2 employed in the present embodiment also includes a connecting portion 23 provided between the sensing portion 21 and the connection portion 22 and exposed to the outside through the lining 131 of the shoe 1. The connecting portion 23 serves to extend the length of the sensing portion 21 to a portion where the circuit block 3 is located, and may be formed integrally with the sensing portion 21 and disposed in the inner space of the lining 131 as shown in FIG. 3.

Examples of the sensor unit 2 that senses static deformation based on the changed in the impedance or capacitance may include a flexible sensor made of a silicon or acrylic polymer (polydimethylsiloxane (PDMS)) to which a functional material (Carbon black, Graphene nanoplatelets, ZnO nanorods, AgNWs, Graphene Oxide, CNT, etc.) is added.

When a functional material such as carbon black is used as a representative example, a physical quantity is measured based on a piezoresistive effect. The piezoresistive effect is largely due to two mechanisms: a tunneling effect and destruction and formation of a conduction path. According to the present embodiment, a mechanism for changing the number of conductive paths within a sensor as an existing conduction path is destroyed or a new conduction path is formed while the flexible sensor is being stretched, that is, a mechanism for destruction and formation of conductive paths, was applied.

In addition to the above mechanisms, there is a driving mechanism of a functional sensor, such as a resistance change mechanism based on a microcontact-reversible effect of silicon rubber filled with a conductive solid (or powder), and a piezotronic mechanism that enables active interactions between a sensor element and a physical stimulus by combining the piezoelectric polarization of a material with the semiconductor properties of the material.

In order to improve the sensitivity of this sensor to deformation caused by the static load of this sensor and environmental factors such as a temperature, there is a method of mixing zinc stannate (ZnSnO3) nanocubes. Because the number of effective conduction paths inside the sensor 2 may be effectively changed when the ZnSnO3 nanocubes are mixed, the sensitivity of a functional material-based sensor may be greatly improved.

The sensing portion 21 of the sensor unit 2, as well shown in an enlarged portion of FIG. 1, includes a silicon-based or acrylic-based polymer material including at least one of carbon black, Graphene nanoplatelets, ZnO nanorods, AgNWs, Graphene oxide, and CNTs described above, so as to smoothly detect an electrical signal generated due to deformation.

The shoe 1 employed in the present embodiment includes a tongue member 14 that covers the top of the wearer's foot, and the tongue member 14 includes a cover part 141 that cover the top of the foot, and an installation part 142 bent from the cover part 141 so that one end of the installation part 142 is detachably coupled to the upper 13 of the shoe 1, the installation part 142 accommodating the circuit block 3.

Here, a coupling means such as a Velcro 142a may be provided in the installation part 142 and a coupling portion to which the Velcro 142a may be coupled is also provided in a portion of the upper 13 corresponding to the installation part 142.

In the present embodiment having such a configuration, the circuit block 3 is installed on a portion other than the cover part 141 or the lining 131 of the upper 13 in contact with the wearer's foot, that is, on the installation part 142, so that the inconvenience of wearing due to the installation of the circuit block 3 may be addressed, and the installation part 142 is configured to be detachably coupled to the outer surface of the upper 13, so that a knot work may be performed without causing interference by the installation part 142 when knotting, for example, a shoelace.

A tension-type smart shoe unit capable of foot pressure measurement according to another embodiment of the present invention will now be described in detail with reference to FIG. 7.

Figure 7:
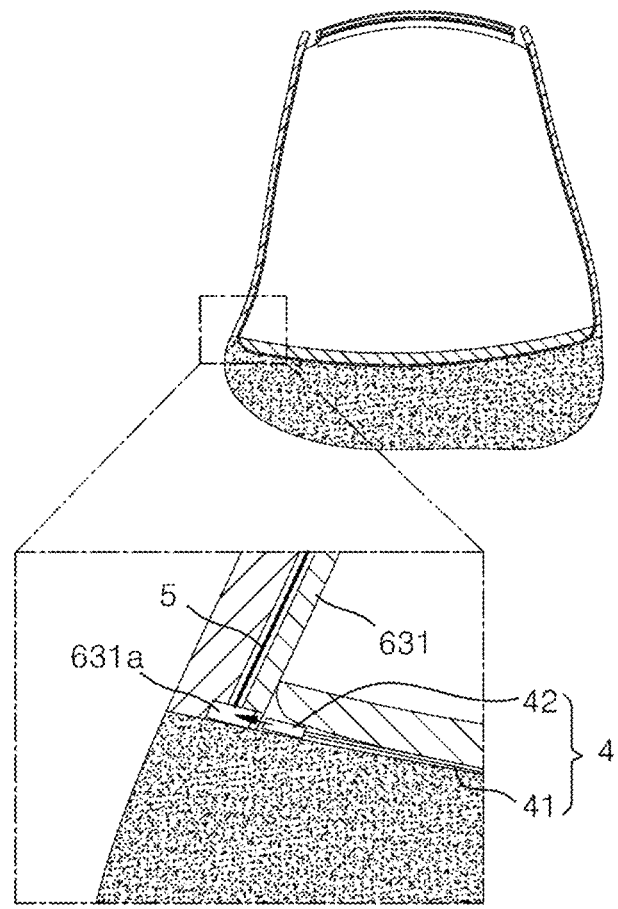
FIG. 7 is a cross-sectional view of a tension-type smart shoe unit capable of foot pressure measurement according to another embodiment of the present invention, the cross-sectional view corresponding to FIG. 2.

FIG. 7 is a cross-sectional view of the tension-type smart shoe unit capable of foot pressure measurement according to another embodiment of the present invention, the cross-sectional view corresponding to FIG. 2.

According to the present embodiment, a lining 631 of a shoe includes a conductive line 5 installed so as to electrically connect a connection portion 42 of a sensor unit 4 to a connecting portion of a circuit block.

The conductive line 5 may be implemented in a wire form or in a ribbon form like a sensing portion 41 of the sensor unit 4, and the lining 631 has an eyelet 631a such as a hole for fixing a shoelace.

In the present embodiment, the eyelet 631a is simply implemented in the form of a through hole formed in the lining 631. However, the present invention is not limited thereto, and, for example, the eyelet 631a may be implemented in the form of a metal having the shape of a round frame coupled to the through hole.

The connection portion 42 of the sensor unit 4 penetrates the eyelet 631a of the lining 631 and is not only electrically connected to the conductive line 5 and but also mechanically firmly fastened to the conductive line 5, and thus the sensing portion 41 may be effectively deformed by foot pressure during walking. In the present embodiment having such a configuration, deformation of the sensing portion 41 of the sensor unit 4 due to disturbances other than foot pressure caused by the wearer's walking, namely, due to disturbances such as ankle twist or walking distortion, may be suppressed, and the connection portion 42 is fixed to the lining 631, which is located as close as possible to a portion on which the walking foot pressure acts, so that the sensing portion 41 of the sensor unit 4 is deformed when the walking foot pressure is relatively completely exerted, whereby the dynamic pressure level during walking or the weight in a stationary state may be precisely measured.

Figure 9:
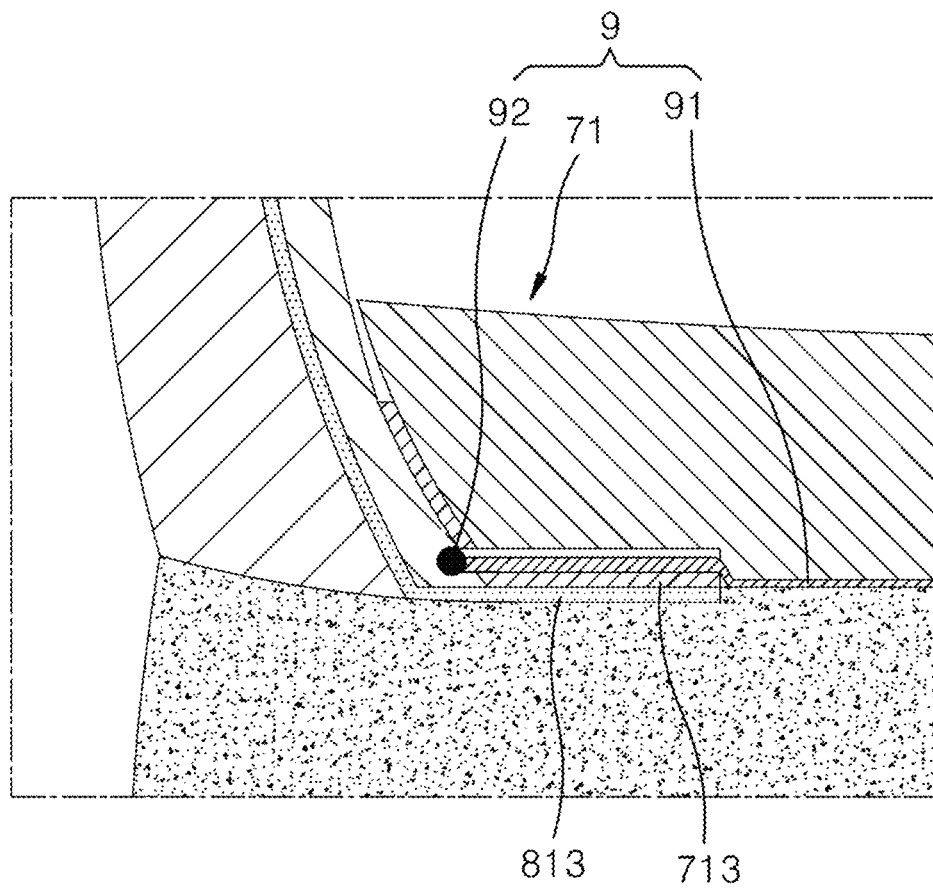
FIG. 9 is a view of another embodiment of the present invention corresponding to an enlarged portion of FIG. 7.

FIG. 8 is a bottom view of a combined state of an insole and a sensor unit employed in a tension-type smart shoe unit capable of foot pressure measurement according to another embodiment of the present invention, and FIG. 9 is a view of another embodiment of the present invention corresponding to an enlarged portion of FIG. 7.

According to the present embodiment, a lining of a shoe includes a lining-side conductive line 813 installed so as to electrically connect a connection portion 92 of a sensor unit 9 to a connecting portion of a circuit block.

As well as shown in (a) of FIG. 8, an insole 71 of the shoe includes a contact portion 711 disposed to face the sole of a wearer so that the sole of the wearer may come into contact with the contact portion 711, and a pair of edge portions 712 disposed to face the midsole of the shoe.

A seating groove 711a on which a sensing portion 91 of the sensor unit 9 is seated is formed between the pair of edge portions 712, so that each of the edge portions 712 has a relatively protruding shape due to the formation of the seating groove 711a.

Each of the edge portions 712 includes an insole-side conductive line 713 connected to the lining-side conductive line 813, and thus, the connection portion 92 of the sensor unit 9 penetrates each of the edge portions 712 and is connected to the insole-side conductive line 713, whereby the sensor unit 9 and the circuit block are connected to each other.

In the present embodiment having such a configuration, due to fixing of the connection portion 92 of the sensor unit 9 to the edge portions 712 of the insole 71, the sensing portion 91 of the sensor unit 9 is deformed in a tensile manner as shown in (b) of FIG. 8 on only the insole 71 on which the walking foot pressure of the wearer is fully exerted, and thus the dynamic pressure level during the wearer's walking or a body weight in a stationary state may be more precisely measured without being affected by noise or disturbances such as deformation due to an influence other than walking foot pressure.

The connection portion 92 of the sensor unit 9 is formed to have a larger outer diameter than a hole of each edge portion 712 so as to be coupled to the hole of each edge portion 712 in a forced fitting manner, so that the connection portion 92 of the sensor unit 9 may be conveniently and efficiently attached to and separated from the insole 71 of the sensor unit 9.

For example, when the connection portion 92 is loosely fastened to the edge portions 712, a deformation value due to walking and weight may not faithfully reflect the original load, and thus may be configured to be firmly fixed to the edge portions 712 by including a structure such as a knot of a shoelace or a structure such as a tick button.

In other words, the structure of the connection portion coupled to the hole in a forced fitting manner by having a larger outer diameter than the hole of the edge portions is not limited to the example shown in FIG. 9, and may be implemented as a structure such as a knot of a shoelace or as a snap coupler such as a tick button.

2) Carbon Nanotube Alignment Method, Aligned Carbon Nanotube Sensor, and Manufacturing Method Therefor A carbon nanotube alignment method according to an embodiment of the present invention will now be described in detail with reference to the accompanying drawings.

Figure 10:
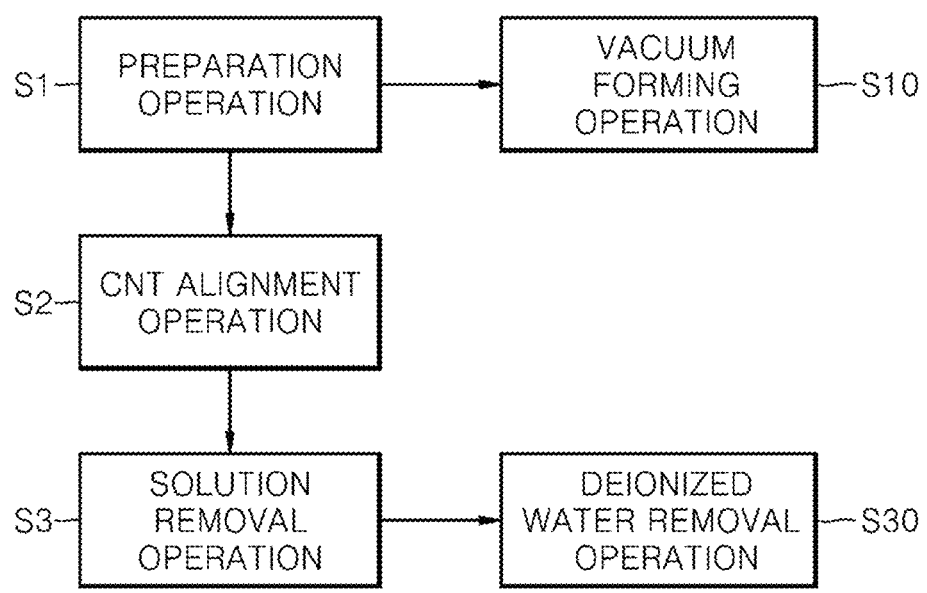
FIG. 10 is a block diagram illustrating a carbon nanotube alignment method according to an embodiment of the present invention.
Figure 12:
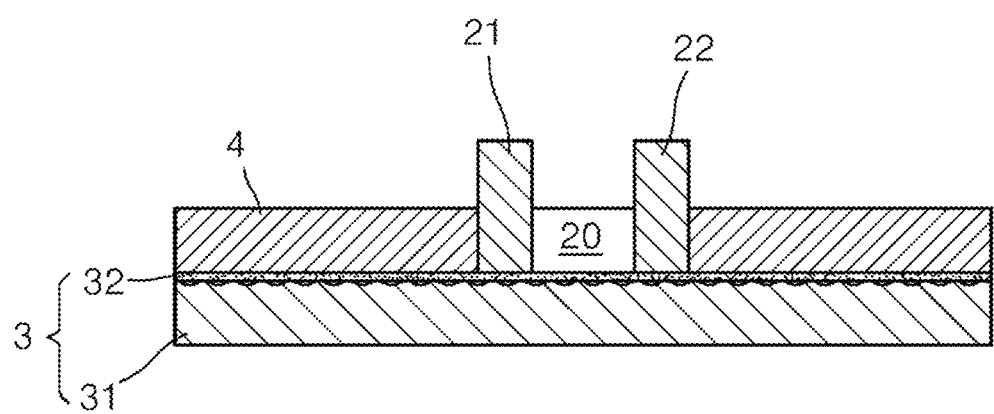
FIG. 12 is a cross-sectional view taken along line XII-XII of FIG. 11.
Figure 13:
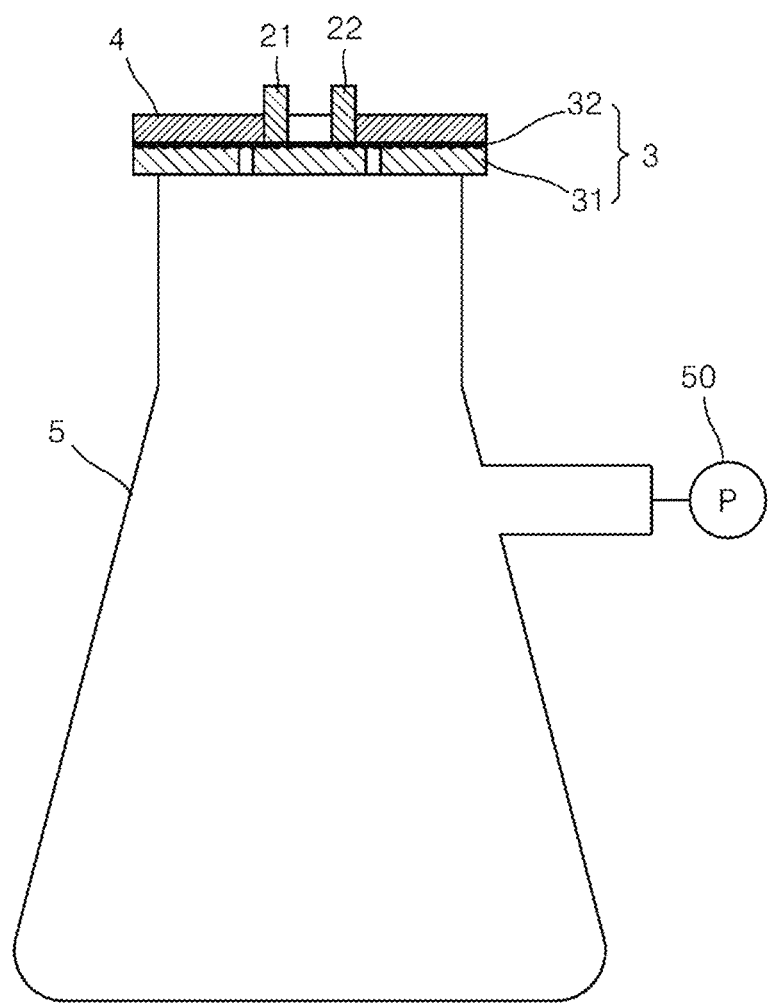
FIG. 13 is a cross-sectional view taken along line XIII-XIII of FIG. 11.

FIG. 10 is a block diagram illustrating a carbon nanotube alignment method according to an embodiment of the present invention, FIG. 11 is a view for explaining respective implementation processes of operations constituting the carbon nanotube alignment method according to an embodiment of the present invention, FIG. 12 is a cross-sectional view taken along line XII-XII of FIG. 11, and FIG. 13 is a cross-sectional view taken along line XIII-XIII of FIG. 11.

As shown in FIG. 10, in a method of aligning carbon nanotubes (CNTs) 1, according to an embodiment of the present invention, the CNTs 1 are aligned in one direction so that even a small number of CNTs 1 may improve sensing sensitivity, and includes a preparation operation S1, a CNT alignment operation S2, and a solution removal operation S3.

As well shown in a block A of FIG. 11 and FIG. 12, in the preparation operation S1, a CNT-containing solution is accommodated in a space 20 between a pair of electrodes 21 and 22 and a substrate 3 on which the electrodes 21 and 22 are placed. The pair of electrodes 21 and 22 are a portion to which a voltage is applied to form an electric field, and the substrate 3 forms a space capable of accommodating a liquid CNT-containing solution, together with the electrodes 21 and 22, and is a portion on which the CNTs 1 remain after the solution removal operation to be described later is performed.

In the present embodiment, as shown in FIG. 12, the space 20 in which the CNT-containing solution is accommodated is primarily formed by a disk 4 having a through slit and made of an insulating material and the substrate 3 placed under the disk 4, and is finally defined by the electrodes 21 and 22 placed on both sides of the through slit and the substrate 3.

In the CNT alignment operation, as shown in a block B and a right enlarged portion of a block C in FIG. 11, an electric field is formed by applying a voltage to the electrodes 21 and 22, and thus the CNTs 1 contained in the CNT-containing solution are aligned in the direction of the electric field.

For example, when the electrodes 21 and 22 are disposed to face each other in a parallel state, electric force lines are formed in a straight line, and thus the CNTs 1 are aligned in a straight line. For example, when the electrodes 21 and 22 are disposed to be orthogonal to each other, electric force lines are formed in a curved line, and thus the CNTs 1 are aligned in a curved line.

As such, the present embodiment has the advantage of aligning the CNTs 1 in a desired direction by variously changing the installation positions of the electrodes 21 and 22 and the strength of the electric field.

In the solution removal operation, only the aligned CNTs 1 remain on the substrate 3 by removing a liquid solution excluding particulate CNTs 1 from the CNT-containing solution. Of course, a method of removing a solution may be implemented in various ways, such as, discharging by a pump.

In a carbon nanotube alignment method according to an embodiment of the present invention having a configuration as described above, after a CNT-containing solution is accommodated in the space 20 between the pair of electrodes 21 and 22 and the substrate 3, an electric field is formed, so that the CNTs 1 are aligned in the direction of electric force lines, and then the solution is removed so that only the CNTs 1 aligned in one direction remain on the substrate 3, and thus the CNTs 1 may be aligned in a desired direction by variously changing the installation location of the electrodes 21 and 22 and the intensity of the electric field even with a simple configuration.

The substrate 3 is a portion where the CNTs 1 remain, and may have various structures. However, in the present embodiment, the substrate 3 includes a base member 31 made of glass and a filter paper 32 placed on the base member 31.

The base member 31 may be implemented as a structure such as frit glass, and the filter paper 32 is placed on the base member 31 to be at a location where it may be in contact with the CNT-containing solution, and may be formed of a porous material so as to have voids via which the solution may be discharged.

The present embodiment includes a vacuum forming operation S10 of forming a vacuum by using a vacuum pump 50 between the base member 31 and the filter paper 32, as shown in FIG. 13, to prevent a solution from being discharged between the filter paper 32 and the base member 31.

Because the CNT-containing solution includes deionized water, a foreign material may be prevented from remaining in the CNTs 1 after deionized water is removed without affecting the polarity of the CNTs 1.

The present embodiment includes a deionized water removal operation S30 for removing such deionized water. In other words, in the deionized water removal operation S30, when the voltage is released after the CNT alignment operation S2, the deionized water is removed using the vacuum pump 50, so that only the aligned CNTs 1 may remain on the filter paper 32.

In this way, when the deionized water is removed by using the vacuum pump 50 employed to form a vacuum between the filter paper 32 and the base member 31, the CNTs 1 aligned with a pumping action by the vacuum pump 50 may be expected to be smoothly adsorbed to the filter paper 32.

The CNTs 1 contained in the CNT-containing solution is preferably used in an amount of less than 0.02 wt % to increase the degree of completeness of alignment and to implement a high-performance sensor function even with a small amount.

Optimal conditions for the alignment of the CNTs 1 may vary depending on the magnitude of the voltage, frequency, and time, but, as a result of an experiment, it was optimal when the voltage is applied at 350 kHz-10 KV for 20 seconds. Of course, when a higher voltage is applied, an optimal frequency range may vary.

Reference numeral 5 in the drawings indicates a container in which deionized water accommodated in the space 20 between the electrodes 21 and 22 and the substrate 3 by a pumping action of the vacuum pump 50 is temporarily accommodated after being discharged via the filter paper 32 by the pumping action of the vacuum pump 50.

An aligned carbon nanotube sensor manufacturing method according to an embodiment of the present invention will now be described in detail.

Figure 14:
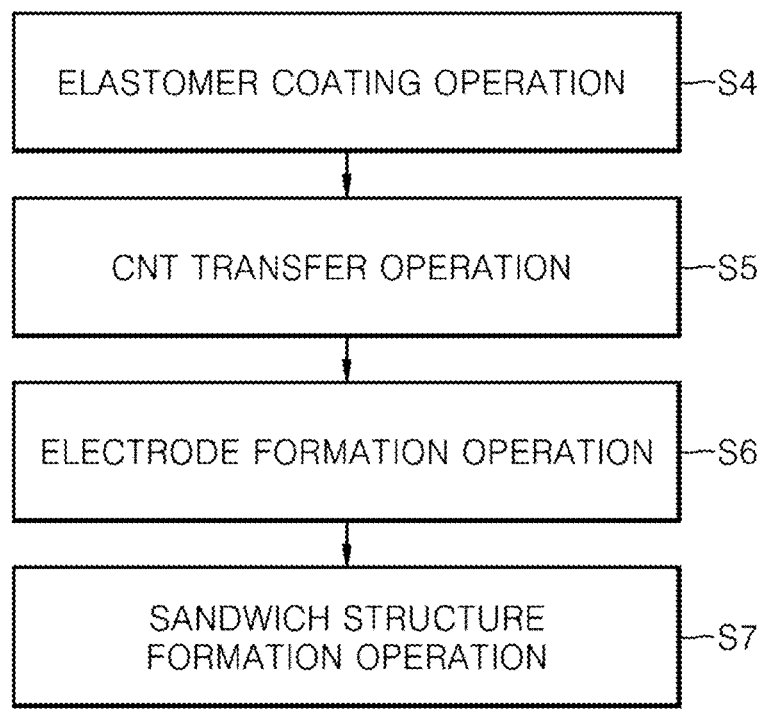
FIG. 14 is a block diagram illustrating an aligned carbon nanotube sensor manufacturing method according to an embodiment of the present invention.
Figure 15:
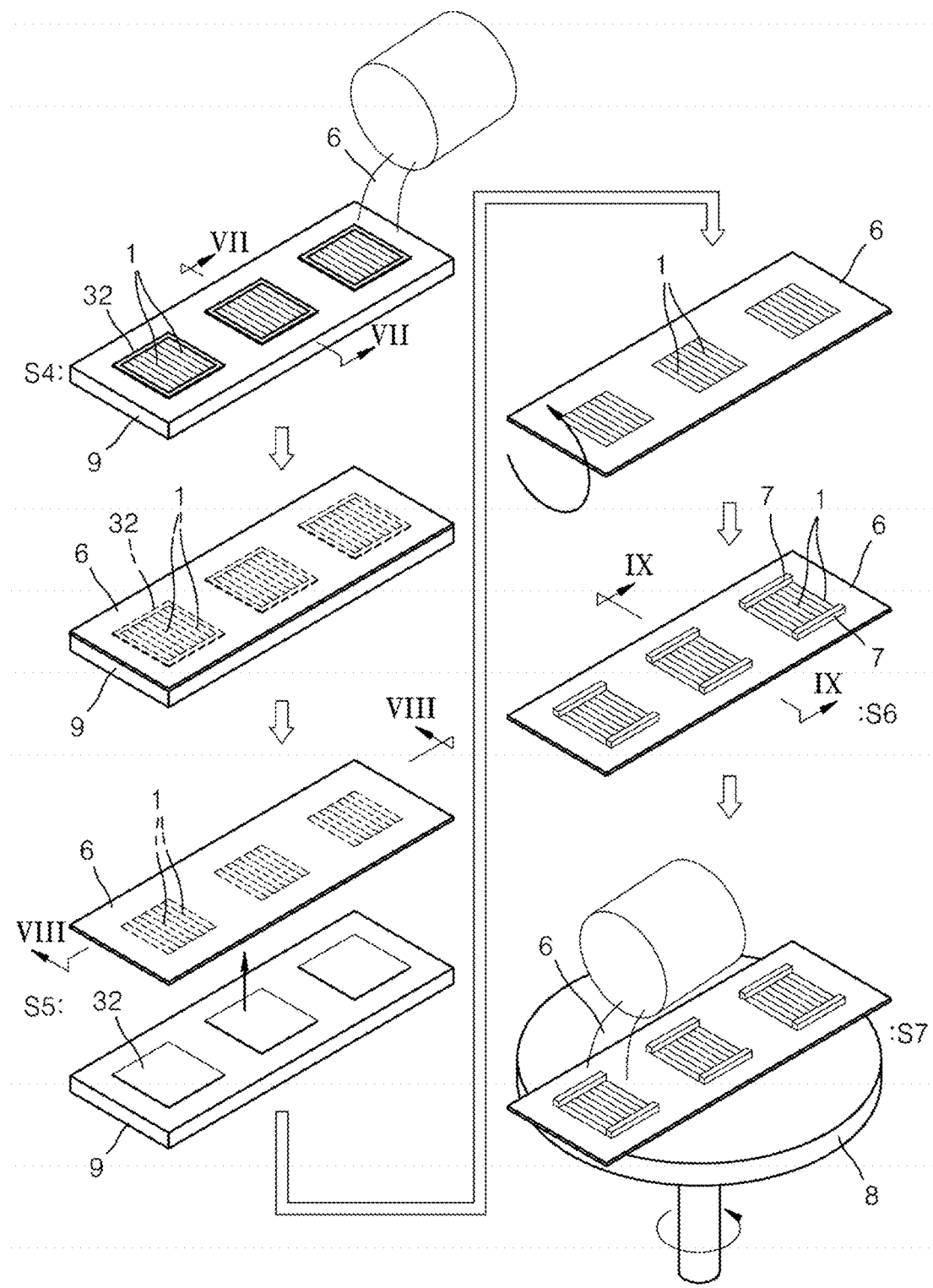
FIG. 15 is a view for explaining respective implementation processes of the operations constituting an aligned carbon nanotube sensor manufacturing method according to an embodiment of the present invention.
Figure 16:
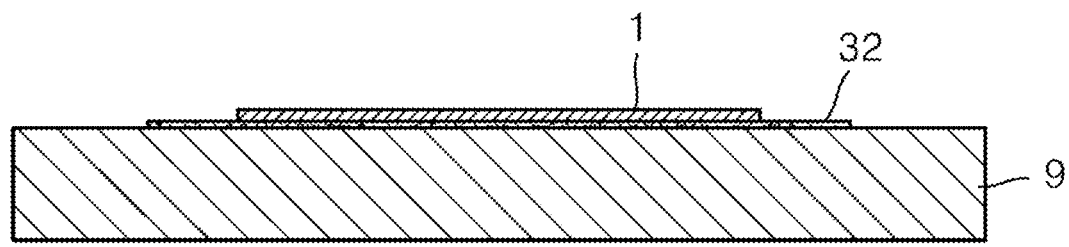
FIG. 16 is a cross-sectional view taken along line XVI-XVI of FIG. 15.
Figure 17:
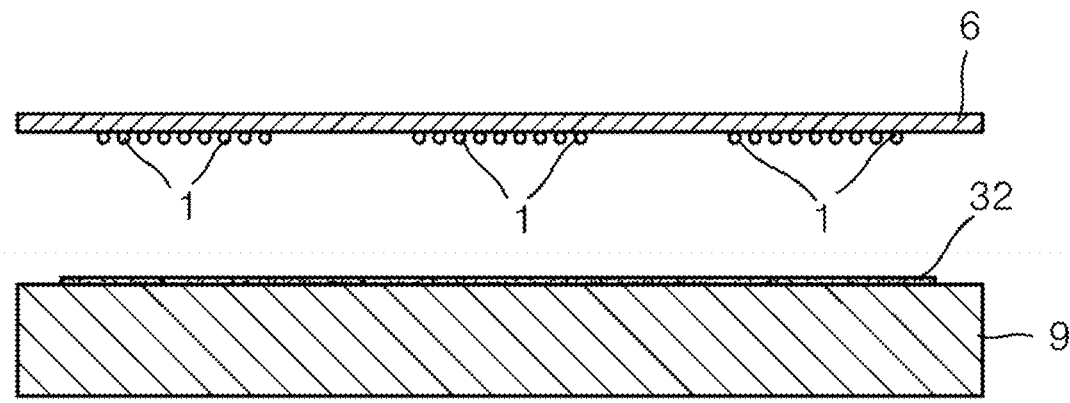
FIG. 17 is a cross-sectional view taken along line XVII-XVII of FIG. 15.
Figure 18:
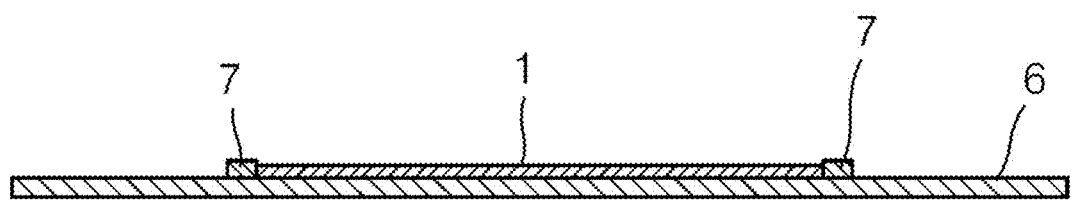
FIG. 18 is a cross-sectional view taken along line XVIII-XVIII of FIG. 15.
Figure 19:
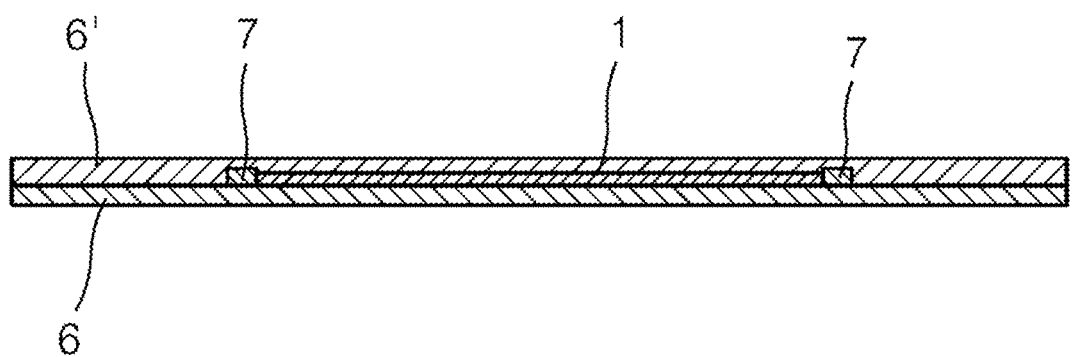
FIG. 19 shows the structure of an aligned carbon nanotube sensor according to an embodiment of the present invention, and is a cross-sectional view of a layer unit for a sensor having a sandwich structure formed by laminating an elastomer on a structure of FIG. 18 by the last process of FIG. 15.

FIG. 14 is a block diagram illustrating an aligned carbon nanotube sensor manufacturing method according to an embodiment of the present invention, FIG. 15 is a view for explaining respective implementation processes of the operations constituting an aligned carbon nanotube sensor manufacturing method according to an embodiment of the present invention, FIG. 16 is a cross-sectional view taken along line XVI-XVI of FIG. 15, FIG. 17 is a cross-sectional view taken along line XVII-XVII of FIG. 15, FIG. 18 is a cross-sectional view taken along line XVIII-XVIII of FIG. 15, and FIG. 19 shows the structure of an aligned carbon nanotube sensor according to an embodiment of the present invention, and is a cross-sectional view of a layer unit for a sensor having a sandwich structure formed by laminating an elastomer on a structure of FIG. 18 by the last process of FIG. 15. As shown in FIG. 14, the carbon nanotube sensor manufacturing method according to an embodiment of the present invention relates to a method of manufacturing a sensor for sensing the movement of the skin or living tissue of a human body (e.g., an eyelid movement, voice detection, pulse, heartbeat, foot pressure, etc.) by using the filter paper 32 on which the CNTs 1 remain, and includes an elastomer coating operation S4, a CNT transfer operation S5, and an electrode formation operation S6.

As shown in FIGS. 15 and 16, in the elastomer coating operation S4, the filter paper 32 on which the CNTs 1 are aligned in one direction is placed on a mold 9, and a liquid elastomer 6 is coated.

A method of aligning the CNTs 1 on the filter paper 32 in one direction is not limited to the above-described carbon nanotube alignment method, and may be implemented in various ways. Of course, the elastomer 6 may be implemented with various materials that may be restored to its original shape after deformation. However, in the present embodiment, polydimethylsiloxane (PDMS) is employed. An acrylic mold may be employed as the mold 9, and the PDMS may be coated on the filter paper 32 to have a thickness of about 100 to 200 μm.

As shown in a left lower end of FIG. 15 and FIG. 17, in the CNT transfer operation S5, after the liquid elastomer 6 is coated, the liquid elastomer 6 is subjected to a curing process, the CNTs 1 are transferred to the cured elastomer 6, and the filter paper 32 is removed. In other words, because the liquid elastomer 6 is viscous, when the liquid elastomer 6 is coated on the filter paper 32 on which the CNTs 1 remain, the remaining CNTs 1 are separated from the filter paper 32, and the liquid elastomer 6 is coupled to the separated CNTs 1 in a transcriptional manner.

In other words, when the liquid elastomer 6 is coated, the liquid elastomer 6 comes into contact with the aligned CNTs 1, and the liquid elastomer 6 and the aligned CNTs 1 adhere to each other during the curing process of the elastomer 6, and, because this adhesive force is generally stronger than an adhesive force between the filter paper 32 and the CNTs 1, the CNTs 1 are naturally transferred to the cured elastomer 6 in the process of removing the filter paper 32. The curing process may be performed in an oven at approximately 60° C. for 8 hours.

Thereafter, when the CNTs 1 are firmly fixed to the elastomer 6 by the curing process and the filter paper 32 is separated from the elastomer 6 in the process of separating the filter paper 32, a sensor structure in which the CNTs 1 remain in the elastomer 6 is formed.

As well shown in the middle right portion of FIG. 15 and FIG. 18, the electrode formation operation S6 is to form an electrode for receiving a signal from the sensor structure manufactured in the above-described CNT transfer operation S5. In the electrode formation operation S6, electrodes 7 are formed on both ends of the CNTs 1 laminated on the elastomer 6, by using a conductive connecting portion such as a metal paste.

In the carbon nanotube sensor manufacturing method according to the present embodiment having such a configuration, the aligned CNTs 1 are transferred to the elastomer 6 by coating the elastomer 6 on the filter paper 32 on which the aligned CNTs 1 remain and curing the elastomer 6, and then the electrodes 7 are formed on both ends of the CNTs 1 to thereby manufacture a sensor that transmits an electrical signal according to deformation. Thus, the sensor may be manufactured with a simple process and at reduced cost, and, by making the alignment direction of the CNTs 1 coincide with the deformation direction of the elastomer 6, a precise sensing function may be realized, and a signal in a non-alignment direction may be blocked, and thus a filter role in a measurement direction may be expected.

As shown in FIG. 19, the present embodiment may further include a sandwich structure formation operation S7 in order to form a sensor of a sandwich structure in which an elastomer 6' is added to the opposite side of the elastomer 6 with the CNTs 1 interposed therebetween.

In other words, in the sandwich structure formation operation S7, the elastomer 6' is additionally formed through a curing process after liquid PDMS is coated on the opposite side of the elastomer 6 with the CNTs 1 interposed therebetween. The added elastomer 6' enables formation of a sensor of a type in which the CNTs 1 are disposed between a pair of PDMS layers by coating liquid PDMS on the CNTs 1 by using, for example, a spin coater 8.

An aligned carbon nanotube sensor according to an embodiment of the present invention will now be described in detail with reference to the accompanying drawings.

FIG. 19 shows the structure of an aligned carbon nanotube sensor according to an embodiment of the present invention, and is a cross-sectional view of a layer unit for a sensor having a sandwich structure formed by laminating an elastomer on the structure of FIG. 18 according to the last process of FIG. 15. As shown in FIG. 19, the aligned carbon nanotube sensor according to the present embodiment includes the elastomer 6 and a CNT unit.

The elastomer 6 is made of an elastically deformable material such as PDMS, as described above, and the CNT unit includes a plurality of CNT monomers 1 and a pair of electrodes 7.

The CNT monomers 1 are spaced apart from each other in a state of being aligned in one direction on the elastomer 6, and each of the electrodes 7 are connected to both ends of the CNT monomers 1 so that the CNT monomers 1 are electrically connected to an external power source, and is formed in the form of a ribbon by a metal paste material.

Figure 21:
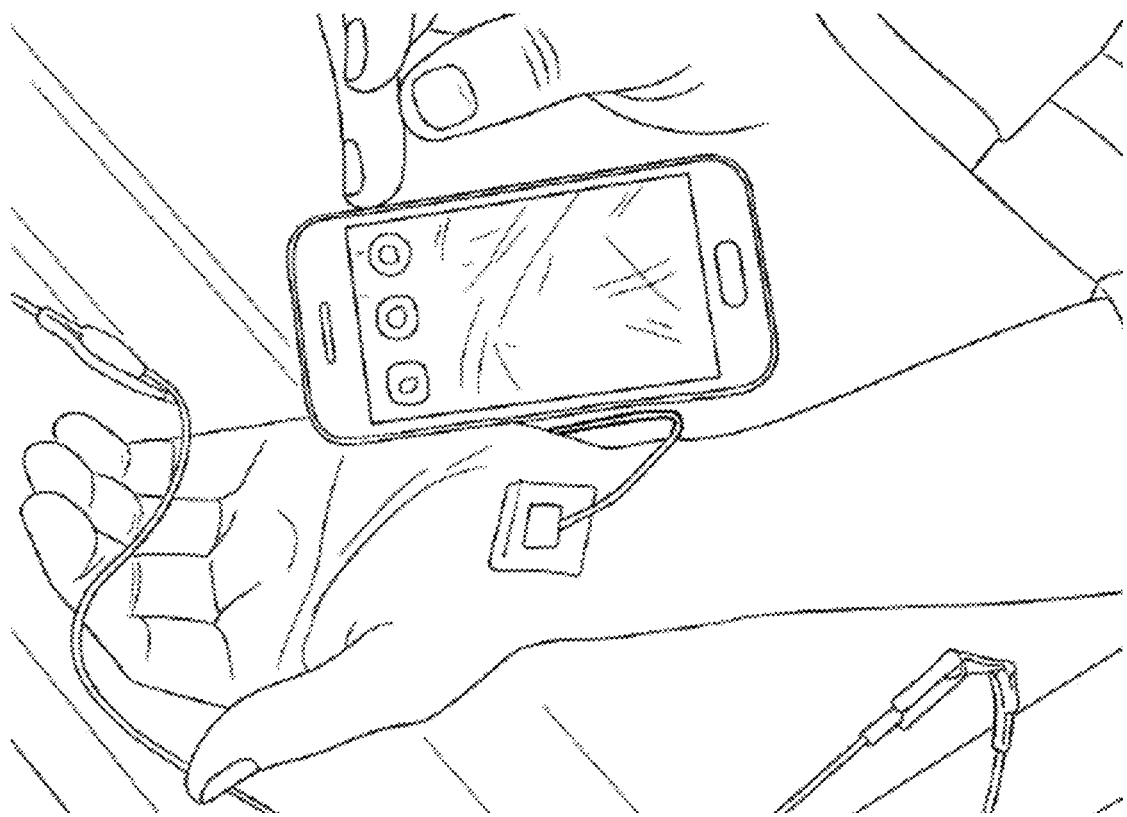
FIG. 21 is a use state view of an aligned carbon nanotube sensor according to an embodiment of the present invention.

In the aligned carbon nanotube sensor according to an embodiment of the present invention having such a configuration, the CNT monomers 1 are aligned in one direction on the elastomer 6 that is deformed according to the movement of a human skin or biological tissue, to be spaced apart from each other, and each of the electrodes 7 for forming a potential difference are connected to both ends of the CNT monomers 1. Thus, an electrical signal according to a minute movement may be sensed, so that health information such as an eyelid movement, voice detection, pulse (refer to a use state view of FIG. 21), heart beating, and foot pressure, may be precisely sensed even with a simple configuration. In addition, a more precise and high-performance sensing function may be implemented by matching the alignment direction of the CNTs 1 with the deformation direction of the elastomer 6.

The present embodiment may include the elastomer 6' that is additionally provided on the opposite side of the elastomer 6 with the CNT unit interposed therebetween and forms a sandwich structure together with the elastomer 6 so that an influence of an external environment upon a sensing function by the CNTs 1 is minimized.

Figure 20:
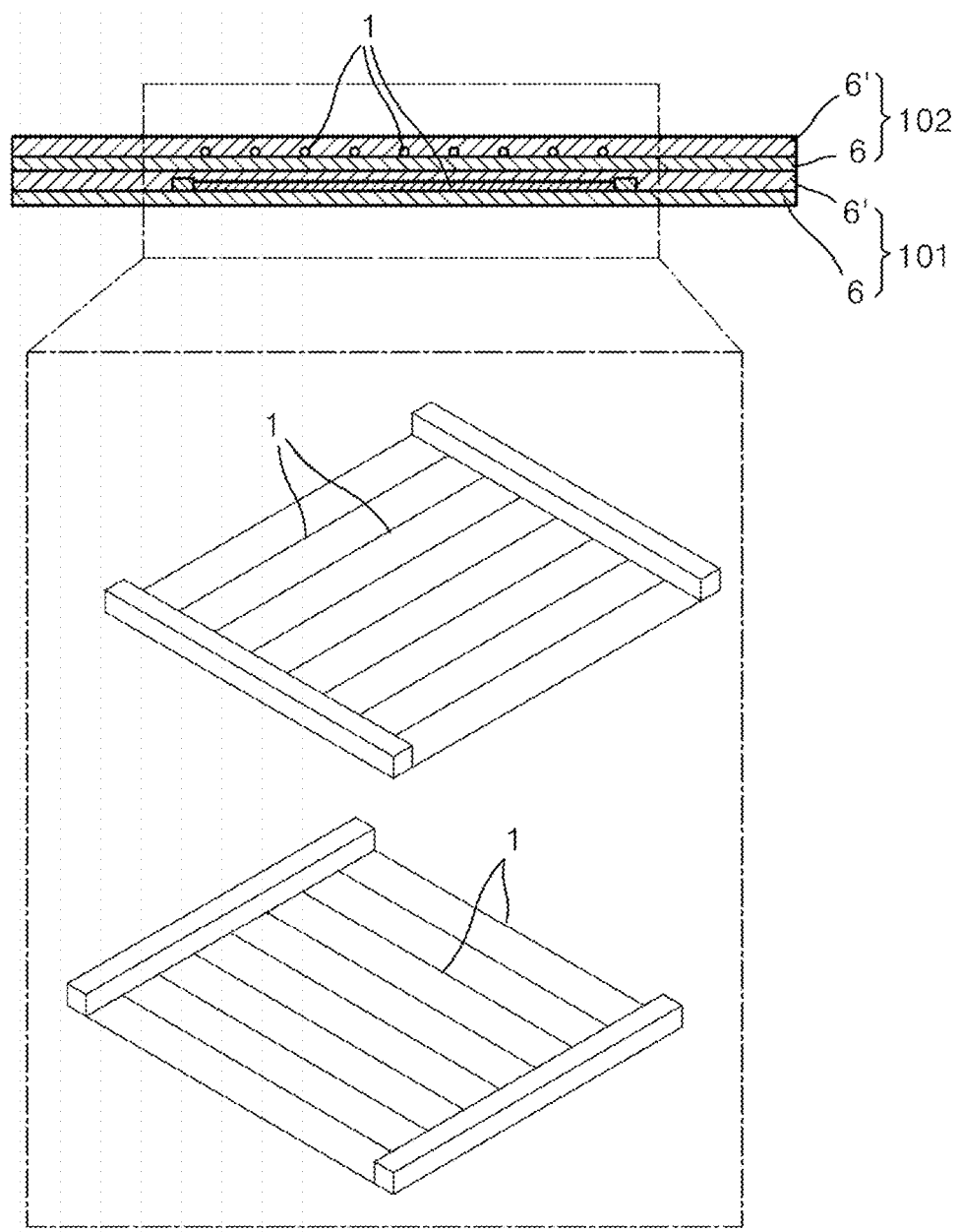
FIG. 20 shows the structure of a carbon nanotube sensor according to another embodiment of the present invention, and is a cross-sectional view of a structure in which a pair of sensor layer units shown in FIG. 19 are stacked in a state where CNT arrangement directions are different from each other.

FIG. 20 shows the structure of a carbon nanotube sensor according to another embodiment of the present invention, and is a cross-sectional view of a structure in which a pair of sensor layer units shown in FIG. 19 are stacked in a state where CNT arrangement directions are different from each other.

In the carbon nanotube sensor according to another embodiment of the present invention, at least two or more layer units 101 and 102 made of a pair of elastomers 6 described above and a CNT monomer 1 provided therebetween are stacked, and the alignment directions of the respective CNT monomers of the layer units 101 and 102 are different from each other.

In other words, the present embodiment includes a first layer unit 101, and a second layer unit 102 having the same configuration as the first layer unit 101 and including CNT monomers 1 arranged in a different direction from the alignment direction of the CNT monomers 1 of the first layer unit 101.

The present embodiment having such a configuration is configured so that the CNT monomers 1 aligned in different directions may be stacked through the elastomers 6 and 6', so that signals according to fine movements of the skin or biological tissue of a human body in various directions may be more precisely sensed.

Figure 22:
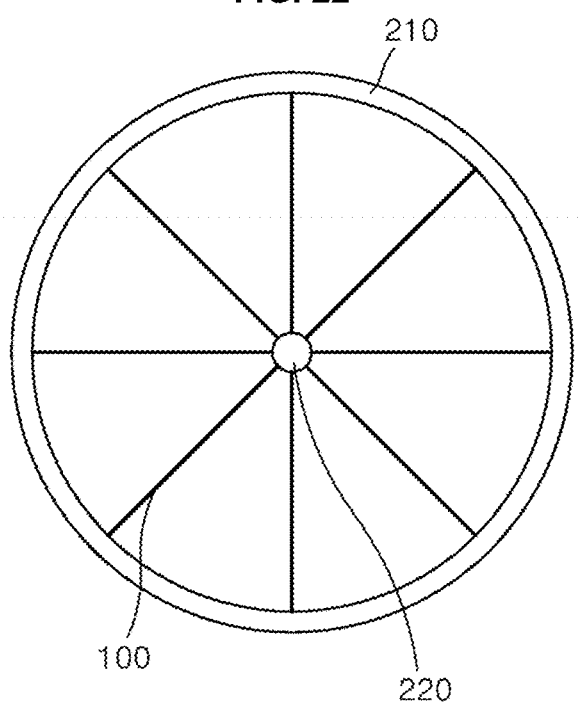
FIG. 22 is a view for explaining a CNT alignment structure according to the electrode arrangement of a carbon nanotube alignment method according to another embodiment of the present invention.

FIG. 22 is a view for explaining a CNT alignment structure according to the electrode arrangement of a carbon nanotube alignment method according to another embodiment of the present invention.

In the present embodiment, unlike the electrode arrangement structure of the previous embodiment, any one electrode 210 among electrodes 210 and 220 is configured in a circular ring shape and the other electrode 220 is placed in the inner center of the electrode, and, accordingly, the alignment direction of carbon nanotubes 100 may be implemented as a radial direction, which is the direction of an electric field.

3) Sensor Using Radially Aligned CNTs, and Sensor Array Unit

A sensor using radially aligned CNTs according to an embodiment of the present invention will now be described in detail with reference to the accompanying drawings.

FIG. 23 is a plan view showing the structure of a sensor using radially aligned CNTs according to an embodiment of the present invention, and FIG. 24 is an operation state view of an embodiment of the present invention.

As shown in FIGS. 23 and 24, the sensor using radially aligned CNTs according to an embodiment of the present invention is capable of sensing the degree of impact or deformation in all directions 360 degrees by using CNT monomers 41, and includes an inner electrode 20, an outer electrode 30, and a plurality of CNT units 40.

The inner electrode 20 is a part for measuring a change in resistance according to occurrence of deformation in the sensor by an external load together with the outer electrodes 30, and is arranged at the center of an arbitrary circle to be separated from the outer electrodes 30 to form a space in which the CNT monomers 41 are placeable.

The outer electrode 30 is arranged on the circumference of the circle to be spaced apart from the inner electrode 20 in a radial direction.

The outer electrode 30 employed in the present embodiment is formed in a ring shape extending in a circumferential direction, so that, even when an impact or pressure is applied to any one of the CNT units 40 arranged in a radial direction, an electrical signal according to the deformation of the CNT unit 40 may be sensed, leading to an improvement in sensing sensitivity.

The CNT units 40 are radially arranged at intervals along the circumferential direction, are disposed between the inner electrode 20 and the outer electrode 30, and include the CNT monomers 41.

The present invention may further include a substrate 10 to which an impact or pressure is applied. The substrate 10, which is a film to which the present sensor has been transferred, may be realized with various materials, but may be preferably formed of an elastically deformable material, such as PDMS, so that the substrate 10 may be restored to its original shape after deformation. In the sensor using radially aligned CNTs according to an embodiment of the present invention having such a configuration, any one electrode (inner electrode 20) among electrodes is disposed at the center of a circle and the other electrode (outer electrode 30) is disposed on a circumferential line, and CNT units 40 in each of which CNT monomers 41 are connected to each other in the radial direction are radially arranged between the pair of electrodes 20 and 30. Thus, when an impact or pressure is applied to a location (A in FIG. 24) on the substrate 10, the CNT monomers 41 together with the substrate 10 are deformed as indicated by a two-dot-dashed line of FIG. 24, and thus resistance is changed due to deformation of the radially arranged CNT units 40, so that the presence or absence of an external load and an impact that have caused the deformation of the sensor may be precisely detected.

In addition, the present embodiment is configured such that deformation in the radial direction, which is the arrangement direction of the CNT monomers 41 of the CNT unit 40, may be sensed, but deformation in the circumferential direction of the CNT unit 40 may not be sensed, and thus, when sensing precision in a specific direction is required, a disturbance signal detected in another direction may be fundamentally blocked, and thus a customized sensor capable of detecting a signal only in a required sensing direction may be manufactured.

FIG. 25 is a view for explaining an operation and merits of a sensor using radially aligned CNTs according to another embodiment of the present invention.

Each CNT monomer 141 employed in the present embodiment may include a conductive material 150 enabling different impedance values (or resistance values) to be output according to deformation.

Although the conductive material 150 may be implemented with various materials, it is preferable that the conductive material 150 may include PEDOT:PSS to improve response characteristics with respect to deformation. In other words, as well shown in an enlarged portion of FIG. 25, the PEDOT:PSS effectively transfers charges within the CNT monomers 141 by maintaining the conductivity of the conductive material 150 even when the CNT monomers 141 are disconnected from one another due to deformation.

A sensor using radially aligned CNTs according to another embodiment of the present invention will now be described with reference to FIGS. 26 and 27.

FIG. 26 is a plan view of a sensor using radially aligned CNTs according to another embodiment of the present invention, and FIG. 27 is a view for explaining merits of another embodiment of the present invention.

Unlike the previous embodiment, an outer electrode 230 employed in the present embodiment includes a plurality of electrode elements intermittently arranged by being spaced apart from each other in the circumferential direction.

In the present embodiment having this configuration, the outer electrodes 230 are intermittently arranged at regular intervals to detect a change in resistance corresponding to different deformation amounts of the CNT units 240 by an external load, so that the single sensor may obtain the effect of multiple sensor groups, and a portion on an application structure (sensor attachment target) to which an impact or pressure has been applied may be clearly identified by analyzing the magnitude of the resistance change.

In addition, according to the present embodiment, as shown in FIG. 26, the outer electrodes 230 are intermittently arranged in the circumferential direction so that sensing is accomplished in a one-to-one correspondence only due to deformation of the CNT units 240 connected to the outer electrodes 230, and thus the same effect as an expensive rosette strain gage R as in the conventional art shown in (a) of FIG. 27 may be obtained by selectively using only sensing data of CNT units arranged in a direction required for analysis as shown in (b) of FIG. 27, without using the expensive rosette strain gage R, and, because CNT unit information in more directions may be utilized, precision of a measured strain may be further improved.

FIG. 28 is a view for explaining a structure of a sensor array unit using radially aligned CNTs, according to an embodiment of the present invention.

In the present embodiment, a plurality of sensors 300 as described above are provided and arranged apart from each other, so that, when an impact or pressure is applied to an arbitrary location on a measurement target structure 310, sensors 300 from which signals are transmitted are selected according to deformation of a CNT unit that is deformed together with the measurement target structure 310, and sensing data of the selected sensors 300 is compared with a detection scenario previously set through repeated experiments to thereby precisely sense where the impact or pressure has occurred.

For example, when the sensor array unit according to the present embodiment is employed in a Taekwondo hogu, a signal magnitude on a location where a strike is made will be different from that on the other locations, and, due to transmission of this signal, a location on the Taekwondo hogu to which the strike has been applied may be precisely sensed.

In order to further increase the sensing precision, outer electrodes 430 of each sensor may include a plurality of electrode elements arranged spaced apart from each other in a circumferential direction, as shown in FIG. 29.

According to this configuration, when an impact occurs in a measurement target structure 410, a point on the measurement target structure 410 where alignment direction extension lines of a CNT unit that generates a largest signal among the signals of CNT units 440 deformed between the respective electrode elements meet one another may be selected as an impact occurrence point A, and thus a point on which an impact or pressure is exerted may be precisely measured.

Although various embodiments of the present invention have been described above, the present embodiments and the drawings attached to the present specification merely show a part of the technical spirit included in the present invention. It will be apparent that modifications and specific embodiments that can be easily inferred by those skilled in the art within the scope of the technical idea are included in the scope of the present invention.

What is claimed is:

1. A sensor comprising:
    an inner electrode arranged at a center of an arbitrary circle;
    an outer electrode spaced apart from the inner electrode in a radial direction and arranged on a circumference of the arbitrary circle; and
    a plurality of carbon nanotube (CNT) units disposed between the inner electrode and the outer electrode, comprising a plurality of CNT monomers arranged in the radial direction, and radially arranged in a circumference direction.

2. The sensor of claim 1, wherein the CNT unit further comprises PEDOT:PSS.

3. The sensor of claim 1, wherein the outer electrode comprises a plurality of electrode elements arranged apart from each other in the circumference direction.

4. A sensor array unit comprising a plurality of sensors of claim 1 that are spaced apart from each other.

5. The sensor array unit of claim 4, wherein the outer electrode of each of the sensors comprises a plurality of electrode elements arranged apart from each other in a circumference direction.

* * * * *